(12) United States Patent
Li et al.

(10) Patent No.: US 8,608,921 B2
(45) Date of Patent: Dec. 17, 2013

(54) LAYERED ENZYME COMPOSITIONS FOR USE WITH ANALYTE SENSORS

(75) Inventors: Xiaolong Li, Granada Hills, CA (US); Rajiv Shah, Rancho Palos Verdes, CA (US); Qingling Yang, Northridge, CA (US); Yiwen Li, Arcadia, CA (US); Barry Phong Pham, Sun Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 235 days.

(21) Appl. No.: 13/010,640

(22) Filed: Jan. 20, 2011

(65) Prior Publication Data

US 2012/0186997 A1 Jul. 26, 2012

(51) Int. Cl.
*G01N 27/327* (2006.01)
*G01N 27/416* (2006.01)

(52) U.S. Cl.
USPC ............ 204/403.11; 204/403.04; 204/403.14; 435/14

(58) Field of Classification Search
USPC ............. 204/403.01–403.15; 205/777.5, 778, 205/792; 435/4–40.52; 422/68.1–98
See application file for complete search history.

(56) References Cited

U.S. PATENT DOCUMENTS

| | | | |
|---|---|---|---|
| 5,312,590 A | 5/1994 | Gunasingham | |
| 2003/0178998 A1* | 9/2003 | Ikura et al. | 324/448 |
| 2005/0272989 A1 | 12/2005 | Shah et al. | |
| 2006/0004272 A1 | 1/2006 | Shah et al. | |
| 2006/0211933 A1* | 9/2006 | Zimmermann et al. | 600/352 |
| 2011/0152654 A1* | 6/2011 | Wang et al. | 600/347 |

OTHER PUBLICATIONS

Sun et al., "Multilayered construction of glucose oxidase and silica nanoparticles on Au electrodes based in layer-by-layer covalent attachment". Biomaterials 27 (2006), pp. 4042-4049.
Wu et al., "Amperometric glucose biosensor based on layer-by-layer assembly of multilayer films composed of chitosan, gold nanoparticles and glucose oxidase modified Pt electrode". Biosensors and Bioelectronics 22 (2007), pp. 838-844.
Zou et al., "Amperometric glucose biosensor prepared with biocompatible material and carbon nanotube by layer-by-layer self-assembly technique". Electrochimica Acta 53 (2008), pp. 4089-4095.
International Search Report dated Apr. 5, 2012 for PCT application No. PCT/US2012/021980 filed on Jan. 20, 2012.

* cited by examiner

*Primary Examiner* — Susan D Leong
(74) *Attorney, Agent, or Firm* — Gates & Cooper LLP

(57) ABSTRACT

Embodiments of the invention provide amperometric analyte sensors having optimized elements such as electrodes formed from sputtered platinum compositions as well as layers of material selected to optimize the characteristics of a wide variety of sensor elements and sensors. While embodiments of the innovation can be used in a variety of contexts, typical embodiments of the invention include glucose sensors used in the management of diabetes.

7 Claims, 14 Drawing Sheets

LAYERED ENZYME COMPOSITIONS FOR USE WITH ANALYTE SENSORS

CROSS REFERENCE TO RELATED APPLICATIONS

This application is related to U.S. patent application Ser. No. 11/633,254; U.S. patent application Ser. No. 12/184,046; U.S. patent application Ser. No. 12/345,354; U.S. patent application Ser. No. 12/572,087; and U.S. patent application Ser. No. 12/643,790, the contents of each of which are herein incorporated by reference.

BACKGROUND OF THE INVENTION

1. Field of the Invention

Analyte sensors (e.g. glucose sensors used in the management of diabetes) and methods and materials for making and using such sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

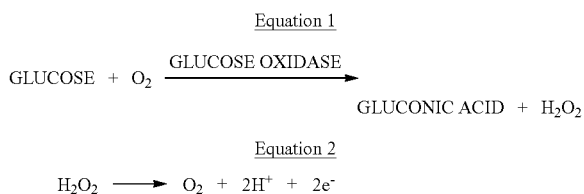

Equation 1

$$\text{GLUCOSE} + \text{O}_2 \xrightarrow{\text{GLUCOSE OXIDASE}} \text{GLUCONIC ACID} + \text{H}_2\text{O}_2$$

Equation 2

$$\text{H}_2\text{O}_2 \longrightarrow \text{O}_2 + 2\text{H}^+ + 2e^-$$

The glucose oxidase is used to catalyze the reaction between glucose and oxygen to yield gluconic acid and hydrogen peroxide (equation 1). The $\text{H}_2\text{O}_2$ reacts electrochemically as shown in equation 2, and the current can be measured by a potentiostat. These reactions, which occur in a variety of oxidoreductases known in the art, are used in a number of sensor designs.

Problems associated with electrochemical sensors include less than ideal sensitivity and signal to noise ratios, particularly at low concentrations of analyte, as well as the degradation of sensor function over time. Consequently, methods and materials designed to address such challenges in this technology, are desirable.

SUMMARY OF THE INVENTION

Amperometric sensors including many glucose sensors used to monitor physiological conditions in diabetic individuals typically comprise a plurality of layered elements formed from different compositions. These layered amperometric sensors can include, for example, one or more electrode layers, interference rejection layers, analyte sensing layers, analyte modulating layers and cover layers etc. Understandably, the compositions used to form the various layers of such sensors can have a profound effect on the performance and functional parameters of these sensors.

As disclosed herein, amperometric sensors comprising a plurality of layers of a oxidoreductase such as glucose oxidase at differing concentrations can generate an $\text{H}_2\text{O}_2$ signal at a sensor electrode that is sufficient to quantify associated glucose levels while simultaneously reducing the likelihood that $\text{H}_2\text{O}_2$ will react with and damage the oxidoreductase. Embodiments of the invention include an amperometric analyte sensor apparatus comprising a base layer, a conductive layer disposed on the base layer and comprising a working electrode coated with a plurality of different layers comprising concentrations of an oxidoreductase such as glucose oxidase. In one illustrative embodiment, a first analyte sensing layer comprising a first concentration of glucose oxidase is disposed on/over the conductive layer (e.g. in direct or indirect contact with the electroactive surface of an electrode). A second analyte sensing layer comprising a second concentration of glucose oxidase is disposed over this first analyte sensing layer and a third analyte sensing layer comprising a third concentration of glucose oxidase is disposed over the second analyte sensing layer. Typically, an analyte modulating layer is then disposed over these first, second and third analyte sensing layers. Permutations of this arrangement include sensors having two analyte sensing layers having different concentration of an oxidoreductase as well as sensors having four, five, six or more analyte sensing layers.

In embodiments of the invention, the first concentration of glucose oxidase is typically greater than the second concentration of glucose oxidase (e.g. at least 5-20 KU greater than the adjacent layer). Similarly, in embodiments of the invention, the second concentration of glucose oxidase can be greater than the third concentration of glucose oxidase. In one illustrative embodiment of the invention, the first concentration of glucose oxidase is between 5 KU/mL to 55 KU/mL (e.g. 35 KU/mL to 55 KU/mL); the second concentration of glucose oxidase is between 5 KU/mL to 55 KU/mL (e.g. 5 KU/mL to 45 KU/mL); and/or the third concentration of glucose oxidase is between 5 KU/mL to 55 KU/mL (e.g. 5 KU/mL to 15 KU/mL). Optionally in these layers, the glucose oxidase is crosslinked to poly(vinyl alcohol)-styrylpyridinium (PVA-SbQ) polymers. In certain embodiments of the invention, a surface of the crosslinked PVA-SbQ analyte sensing layer comprises chemical moieties further crosslinked by a plasma deposition process. Optionally the thickness of the first analyte sensing layer is between 0.5 and 1.5 microns, the thickness of the second analyte sensing layer is between 0.5 and 1.5 microns; and/or the thickness of the third analyte sensing layer is between 0.5 and 1.5 microns.

These analyte sensors can further comprising one or more additional elements such as an electrolyte retaining layer, a protein layer, an interference rejection membrane, an adhesion promoting layer; and/or a cover layer disposed over the analyte sensor apparatus, wherein the cover layer comprises an aperture positioned on the cover layer so as to facilitate an analyte present in the mammal contacting and diffusing through an analyte modulating layer; and contacting the analyte sensing layer. In certain embodiments, the working electrode comprises a sputtered platinum composition and the sensor apparatus further comprises an electrolyte retaining layer in operable contact with the conductive layer, wherein the electrolyte retaining layer is formed from a composition selected to absorb 10% to 50% water by weight. Optionally, the analyte modulating layer comprises a blended mixture of a linear polyurethane/polyurea polymer and a branched acrylate polymer blended together at a ratio of between 1:1 and 1:20 by weight %. In certain embodiments of the invention, the analyte modulating layer exhibits a permeability to glucose that changes less than 2% per degree centigrade over a temperature range of 22 to 40 degrees centigrade.

Another embodiment of the invention is a method of modulating a flux of hydrogen peroxide molecules within a layered glucose sensor apparatus, the method comprising organizing layers in the apparatus to comprise a base layer, a conductive layer disposed on the base layer and comprising a working electrode (e.g. one comprising a sputtered platinum composition), a first analyte sensing layer disposed on the conductive layer and comprising a first concentration of glucose oxidase, a second analyte sensing layer disposed over the first analyte sensing layer and comprising a second concentration of glucose oxidase, a third analyte sensing layer disposed over the second analyte sensing layer and comprising a third concentration of glucose oxidase, and an analyte modulating layer disposed over the first, second and third analyte sensing layers. In such embodiments of the invention, the first, second and third concentrations of glucose oxidase within the first, second and third analyte sensing layers function to alter an angle of the flux of hydrogen peroxide molecules in the first second and third layers that is generated by glucose oxidase in the presence of glucose (e.g. as compared to a single layer or concentration of glucose oxidase) so that the flux of hydrogen peroxide molecules within the layered glucose sensor apparatus is directed to the electroactive surface of the working electrode.

Yet another embodiment of the invention is a composition of matter comprising a metallic electrode, a first analyte sensing layer disposed over the metallic electrode and comprising a first concentration of glucose oxidase, a second analyte sensing layer disposed over the first analyte sensing layer and comprising a second concentration of glucose oxidase, a third analyte sensing layer disposed over the second analyte sensing layer and comprising a third concentration of glucose oxidase and an analyte modulating layer disposed over the first, second and third analyte sensing layers.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

As shown in FIG. 5, the working electrode oxidation window for H2O2 is approximately from 500 mv to 800 mv. The background current during that range for Pt black is significantly higher in the group. Background current for pure Pt wire also appears higher is due to a bigger surface area, 6 times of standard sputtered Pt. The surface area of Pt black is also much higher than sputtered working electrode (WE), which could be the reason for higher background current. For sputtered WE the background currents are all significantly lower and they basically fall within the same magnitude.

As shown in FIG. 6, Pt black did not show significantly higher electro-catalytic activity although a much higher background current.

As shown in FIG. 7, interference from acetaminophen for sputtered Pt is lower overall. Pure Pt wire appears higher could be due to a higher surface area. But for Pt black the interference is significantly higher comparing the Isig level to H2O2.

FIG. 8A, shows the results of a sensor in vitro test using a bicarbonate testing system at a temperature range of 36~37 C. The data in FIG. 8A shows sensor Isig with different glucose concentrations (40 na for 2.5 mg/dl glucose, 80 for 5.0 mg/dl, and 120 for 7.5 mg/dl), data providing evidence that sensor linearity is appropriate. FIG. 8B provides modeling data showing comparisons of glucose diffusion profiles with the various layered GOx compositions. FIG. 8C provides modeling data showing a comparison of H2O2 flux(angles) of various layered GOx compositions. The x-axis in FIGS. 8B and 8C comprises the thickness of the layer (with the dotted lines being the layers junctions) and the y-axis comprises the concentrations of glucose and hydrogen peroxide respectively (in mole/m$^3$). FIG. 8D shows sensor current values for of various layered GOx compositions having different enzyme concentration, based on the sensor current value calculation.

DETAILED DESCRIPTION OF THE EMBODIMENTS

Figure 1:
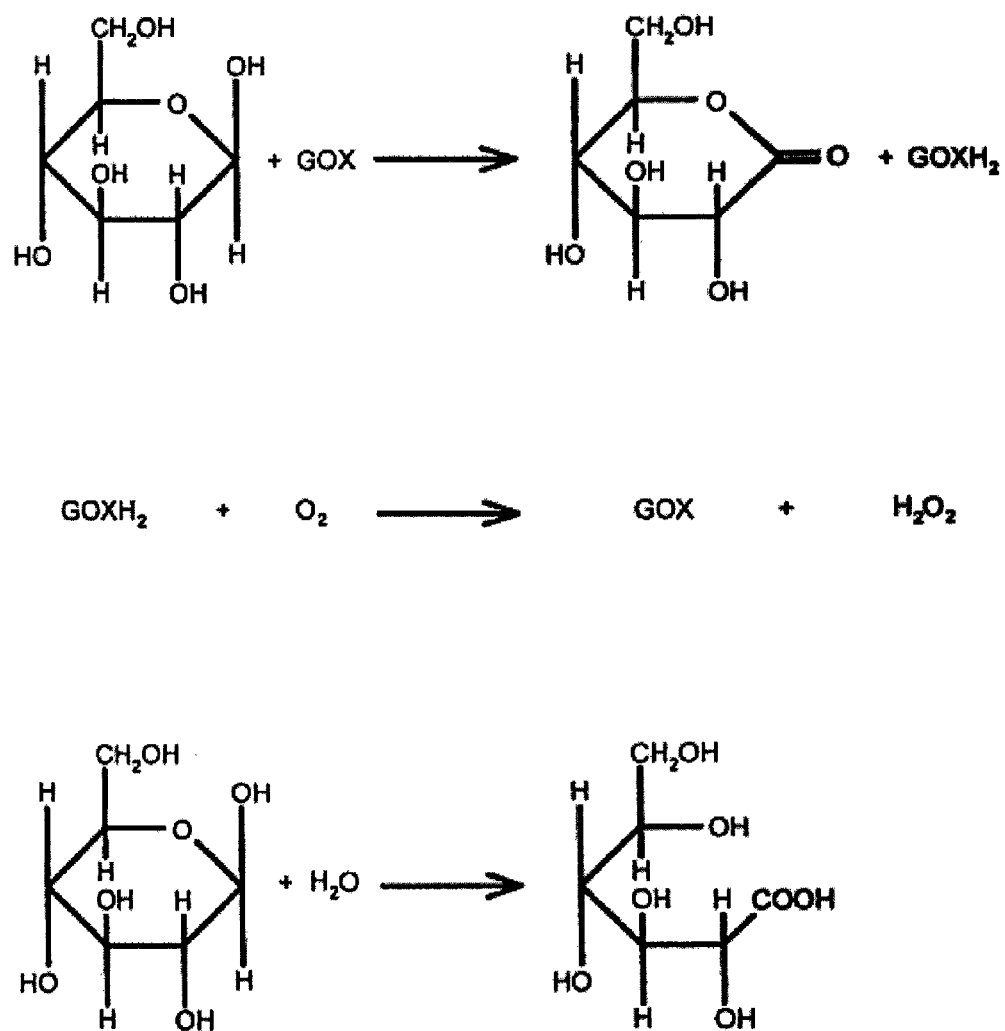
FIG. 1 provides a schematic of the well known reaction between glucose and glucose oxidase. As shown in a stepwise manner, this reaction involves glucose oxidase (GOx), glucose and oxygen in water. In the reductive half of the reaction, two protons and electrons are transferred from β-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "a layer" can include a plurality of layers and equivalents thereof known to those skilled in the art, and so forth. All numbers recited in the specification and associated claims that refer to values that can be numerically characterized with a value other than a whole number (e.g. the amount of a compound) are understood to be modified by the term "about".

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The terms "interferents" and "interfering species/compounds" are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured so as to produce spurious signals.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

As discussed in detail below, embodiments of the invention relate to the use of an electrochemical sensor that exhibits a novel constellation of elements including sputtered platinum working electrode compositions, electrolyte retaining membranes and/or analyte sensing layers that alone, and further in combination, exhibit a unique set of technically desirable material properties. The electrochemical sensors of the invention are designed to measure a concentration of an analyte of interest (e.g. glucose) or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise one or more membrane layers surrounding the enzyme through which an analyte migrates. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their biospecificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391,250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. working electrode compositions) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

Specific aspects of embodiments of the invention are discussed in detail in the following sections.

I. Typical Elements, Configurations and Analyte Sensor Embodiments of the Invention A wide variety of sensors and sensor elements are known in the art including amperometric sensors used to detect and/or measure biological analytes such as glucose. Many glucose sensors are based on an oxygen (Clark-type) amperometric transducer (see, e.g. Yang et al., Electroanalysis 1997, 9, No. 16: 1252-1256; Clark et al., Ann. N.Y. Acad. Sci. 1962, 102, 29; Updike et al., Nature 1967, 214,986; and Wilkins et al., Med. Engin. Physics, 1996, 18, 273.3-51). A number of in vivo glucose sensors utilize hydrogen peroxide-based amperometric transducers because such transducers are relatively easy to fabricate and can readily be miniaturized using conventional technology.

Amperometric sensors including many commercial glucose sensors that are used to monitor physiological conditions in diabetic individuals comprise a plurality of layered elements formed from different compositions. These layered amperometric sensors typically include, for example, one or more electrode layers, analyte sensing layers, analyte modulating layers etc. Understandably, the compositions used to form the various layers in such sensors can have a profound effect on the performance and functional parameters of these sensors. Illustrative general embodiments of such sensors are shown in FIG. 2. While single layers are typically discussed (as the sensor embodiments typically need at least one layer), embodiments having multiple layers (e.g. multiple analyte sensing layers) are also contemplated. The following disclosure describes a variety of elements and illustrative sensor embodiments having different constellations of these elements. In this context, those of skill in the art will understand that one or more sensor elements shown in a first illustrative sensor embodiment disclosed herein can be added to, and/or substituted for elements in a second illustrative sensor embodiment disclosed herein in order to generate further sensor embodiments of the invention.

Sensors Comprising Sputtered Pt Compositions

Metal compositions used to form electrodes in amperometric analyte sensors can include various forms of platinum (Pt). A common form of Pt used to make such electrodes is a bare form of Pt made from premade source such as Pt wire. The art teaches that bare Pt compositions can have a number of desirable electrochemical characteristics including its electrical potential profile, background current, and Isig level. Pt black formed via processes such as electrodeposition is another platinum compositions used to form electrodes in amperometric analyte sensors. Advantages of Pt black include their high 3-D surface area which can produce a high current signal.

As is known in the art, "sputtering" is a process whereby atoms are ejected from a solid target material due to bombardment of the target by energetic particles. It is commonly used for thin-film deposition, etching and analytical techniques. As disclosed herein, a sputtered platinum material has been fabricated and observed to be a superior composition for forming working electrodes in certain sensor embodiments such as implantable glucose sensors that are used to monitor hypoglycemic conditions in diabetic individuals. The combination of this sputtered platinum (Pt) material with additional layers of material selected to optimize the characteristics of this Pt compositions (e.g. "electrolyte retaining membranes") generates sensors having a constellation of elements designed to optimize the in vitro and in vivo performance of the sensor in a variety of contexts. Sensors having this constellation of elements are observed to have a number of highly desirable electrochemical characteristics including a low background current as well as a relatively high sensitivity. Simultaneously these sensor embodiments exhibit relatively low interference responses and system noise levels. Such sensors can be used for example to more accurately measure low glucose ranges in hypoglycemic patients due to their low background current and low noise level.

Sputtered platinum compositions exhibit a constellation of material properties that differ from both electrodeposited platinum black compositions as well as bare Pt compositions (e.g. Pt. wire, disc, foil or the like). For example, sputtered platinum compositions exhibit unique surface structures and morphologies, material properties that have a direct effect on the electrochemical properties of such compositions (see, e.g. Slavcheva et al., Applied Surface Science 255 (2009) 6479-6486; and Mailley et al., Bioelectrochemistry 63 (2004) 359-364, the contents of which are incorporated herein by reference). Sputtered Pt films can be formed to possess platinum particle structures with distinct orientations (e.g. [1 1 1]). Such material properties that are observed with sputtered Pt compositions are unique to platinum compositions formed by this process and are not observed with bare Pt compositions or Pt black compositions (e.g. as formed via electrodeposition processes).

As disclosed herein, when compared to working electrodes formed from electrodeposited Pt black compositions, working electrodes formed from sputtered Pt compositions are observed to yield a much lower background current and exhibit a higher Isig level. In addition the Isig is higher in electrodes formed from sputtered Pt compositions than electrodes of the same geometry and size that are formed from bare Pt. Without being bound by a specific scientific theory or principle, it is believed that the surface of electrodes formed from sputtered Pt compositions do not exhibit simple 2-D flat surfaces (i.e. as occurs with electrodes formed from bare Pt compositions), a phenomena which explains why the Isig is higher than expected. As discussed in detail below, associated electrolyte retaining layers/membranes/matrices have further been developed to optimize the in vitro and in vivo performance of working electrodes formed from sputtered Pt compositions (e.g. by facilitating the conduction of electrical signals within the sensor).

Embodiment of the invention include for example, a constellation of elements including a working electrode formed from the sputtered Pt compositions, an interference rejection membrane (IRM) and/or electrolyte retaining membrane, an immobilized glucose oxidase (GOx) layer/membrane with human serum albumin membrane coverage as well as a diffusion control membrane. In one embodiment of the invention comprising a glucose sensor, the sensor in vitro performed at a zero background current, sensitivity at 5-10 nA/100 mg/dL glucose level, with a linearity range up to at least 400 mg/dL. In this embodiment, the sensor Isig level can be raised up to 20 nA/100 mg/dL by adjusting the electrode area or, alternatively, glucose limiting membrane permeability while simultaneously maintaining a low background current. In vivo this glucose sensor embodiment exhibits low noise, good sensor by sensor consistency, quick start-up times and good accuracy. A significant advantage of sensors having these characteristics is high accuracy at the lower glucose range for hypoglycemic patient for a better glucose level monitoring and control due to a low background current and low noise level. Other advantages include a more stable Isig and longer sensor lifetime.

As noted above, a sputtered platinum (Pt) material has been fabricated and adapted to provide a superior composition for working electrodes in analyte sensors such as glucose sensors. Combinations of this sputtered platinum material with materials selected to optimize the characteristics of such Pt compositions provide sensor embodiments having a constellation of elements that optimize the in vitro and in vivo performance of the sensors in a variety of contexts. Sensor embodiments having this constellation of elements are observed to have a low background current and a relatively high sensitivity. In addition, embodiments of this sensor exhibit relatively low interference responses and system noise levels. Embodiments of the invention can be used, for example, to facilitate the measurement of low glucose ranges in hypoglycemic patients. The sputtered platinum compositions can be formed to a variety of thicknesses, for example between 200, 300, 400, 500, 600, 700, 800 900 or 1000 Angstroms. Moreover, in certain embodiments of the invention, the physical aspect of Pt grain size are manipulated (e.g. lower temperature and higher process gas flow-rate while sputtering) so as to control the roughness of the sputtered platinum produced by this process.

The invention disclosed herein has a number of embodiments. One illustrative embodiment of the invention is an amperometric analyte sensor apparatus comprising a base layer; a conductive layer disposed on the base layer and comprising a working electrode, wherein the working electrode comprises a sputtered platinum composition. This sensor embodiment further includes an electrolyte retaining layer in operable contact with the sputtered Pt composition on the conductive layer, wherein the electrolyte retaining layer is formed from a composition selected to absorb 10% to 50% water by weight; an analyte sensing layer disposed over the conductive layer; and an analyte modulating layer disposed over the analyte sensing layer. Optionally in such embodiments, the sputtered platinum composition exhibits a root-mean-square roughness value below 3 nanometers. In certain embodiments of the invention, the analyte sensing layer (or layers) comprises glucose oxidase (e.g. a 5 to 10 um layer comprising GOx at a concentration level of 10 KU to 55 KU/mL). Optionally the sensor comprises 2-3 analyte sensing layers applied via a process such as spin coating (e.g. a 200 rpm spin coating).

As is known in the art, sensors having unobtrusive architectures (e.g. small or thin sensor designs) are highly desirable. For example, because small or thin sensor designs adapted for use in vivo use as technologies are typically less painful to insert than larger sensors, are less obtrusive and easier to use than larger sensors, and are less likely to be dislodged as compared to larger sensors due to their small profile, such streamlined designs are more desirable to sensor users than are larger and/or bulkier sensors. As discussed below, embodiments of the invention comprise electrolyte retaining layers that are thinner than equivalent sensor layers described in the art (see, e.g. U.S. Patent Application 2010/0145172).

Embodiments of the invention can use a variety of compositions as electrolyte retaining layers. For example, certain embodiments of the invention use compositions that function as relatively thin layers, for example electrolyte retaining layers that are not more than 1-7 µm thick (e.g. a single layer that is not more than 1, 2, 3, 4, 5, 6 or 7 µm in thickness applied by a process such as spin coating). In typical embodiments, the electrolyte retaining layer is not more than 3, 4, 5, 6 or 7 µm thick. Such thin layers are desirable in embodiments of the invention where a small and unobtrusive sensor profile facilities its use, for example in vivo glucose sensors where a small sensor is typically both more comfortable for the user and less likely to become dislodged.

In specific embodiments of the invention, the electrolyte retaining layer can comprise a single layer that is 3-7 um thick, (e.g. one applied to the sensor structure via a spin coating process). In certain sensor embodiments, this layer can comprise human serum albumin (HSA) or bovine serum albumin (BSA), typically at a concentration of 5-10% in combination with a hydrophilic polymer such as methyl cellulose, a higher molecular weight poly vinyl pyrrolidone, where the hydrophilic polymer content is typically 1% to 15%, more typically 5% to 12% of the solid matrix weight. One composition for use as a thin electrolyte retaining layer comprises a polypeptide such as glucose oxidase of a serum albumin (e.g. 1, 5, 10 or 15% BSA or HSA) combined with one or more water soluble polymers such as: a high molecular weight methyl cellulose (e.g. above 300,000 Daltons); a polyvinylpyrrolidone (PVP); or a vinylpyrrolidone comonomer such as a vinylpyrrolidone-vinyl acetate comonomer. In this context, by incorporating selected comonomers into the vinylpyrrolidone polymer chain, specific product properties of the homopolymer can be reinforced or weakened, for example by the partial incorporation of less hydrophilic comonomers, such as vinyl acetate, thus obtaining poly vinylpyrrolidone-vinyl acetate (PVP-VA) comonomers. In embodiments of the invention, the hydrophilic polymer content can be between 1 and 15% (e.g. between 5 to 12%) of the solid main matrix weight. One illustrative composition is made by combining 4 g of 10% BSA with 0.2 mL of 1% MC or 0.1 mL of 5% PVP or PVP-VA).

Another composition for use as an electrolyte retaining layer comprises a non-crosslinked hydrophilic polyurethane (PU) having a lower than 30% H2O absorption and 12% less linear expansion (e.g. Hydromed D7 from Cadiotech International). One such composition is made by combining 1-3% PU in 95% Alcohol and 5% H2O. Another composition for use as an electrolyte retaining layer (e.g. one 1.0 µM in thickness) comprises a pHEMA based with silane crosslinked IRM as disclosed herein in combination with a surfactant such as Pluronic F68. One such composition is made by combining 20 g or a 0.7% pHEMA IRM composition with 0.2 g of 1% Pluronic F68. Another composition for use as an electrolyte retaining layer comprises a crosslinked polylysine composition as disclosed herein (e.g. one using polylysine polymers having a molecular weight between 10,000 and 400,000 Daltons) in combination with crosslinked entrapped MC, PVP or PVP-VA. One such composition is made by combining 4 g 1% polylysine with 0.1 g 1% MC, 0.1 g 5% PVP or PVP-VA. Another composition useful in an electrolyte retaining layer comprises a poly(vinyl alcohol)-styrylpyridinium compound (PVA-SbQ), a water-soluble photosensitive polymer useful to entrap and/or encapsulate polymers and enzymes such as glucose oxidase. One illustrative composition comprises a UV crosslinked PVA-SbQ polymer matrix that entraps a water soluble polymer such as PVP, PVP-VA or MC. One such composition is made by combining 5 mL 2% PVA-SbQ with 0.2 mL 1% MC, 0.1 mL 5% PVP or PVP-VA.

In certain embodiments of the invention, water soluble photosensitive poly(vinyl alcohol)-styrylpyridinium (PVA-SbQ) polymers are used to entrap or encapsulate polypeptides (e.g. glucose oxidase and/or human and/or bovine serum albumin) within a matrix that comprises one or more of the layers within a layered sensor architecture (e.g. a protein layer, an electrolyte retaining layer, an analyte sensing layer etc.). PVA-SbQ is a hydrophilic polymer comprising polyvinyl alcohol (PVA) acetalized with N-methyl-4-(p-formyl styryl) pyridinium methosulfate (SbQ). As is known in the art, SbQ groups on such molecules are crosslinked when exposed to UV light (see, e.g. U.S. Pat. Nos. 7,252,912 and 6,379,883). UV-cross-linking of such polymers provides a simple process for the entrapment of polypeptides (e.g. glucose oxidase) within the crosslinked polymer matrix. UV-cross-linking avoids the use of other chemicals such as cross-linker and reaction initiators, and thus avoids the problems of introducing potentially toxic materials into implantable devices such as analyte sensors. Consequently, there is less concern for potential side reactions caused by chemical cross-linking. Moreover, the UV-cross-linking reaction is a simple process that can be controlled both spatially and temporally, as one may selectively cross-link the particles by limiting the amount of UV irradiation to certain areas for selected time periods. Embodiments of the invention comprise sensor layers made from this material, embodiments which can eliminate the need for the use of other cross linkers (such as glutaraldehyde) in glucose sensor fabrication. In embodiments of the invention, GOx can be coupled to this matrix to generate sensors having analyte sensing layers that result in enhanced Isig quality in regards to sensor stability, linearity and diminished noise levels. In certain embodiments of the invention, this matrix functions as an electrolyte retaining layer.

A variety of methods and materials relating to the use of poly(vinyl alcohol)-styrylpyridinium (PVA-SbQ) polymers to entrap or encapsulate molecules are known in the art. See, e.g. Moser et al., Biosensors and Bioelectronics 17 (2002) 297-302; Chang et al., Biosensors and Bioelectronics 17 (2002) 1015-1023; Sohn et al., Sensors and Actuators, B, Vol. 41, pp. 7-11, 1997; Vering et al., Analyst, 1998, Vol. 123 (1605-1609); Pourciel et al. Sensor and Actuators B 94 (2003) 330-336; and U.S. patent publication No. 7,415,299 and 20070023286, the contents of which are incorporated by reference. In one illustrative embodiment of an analyte sensing layer and/or a electrolyte retaining layer of the invention, a PVA-SbQ polymer can be mixed with a phosphate buffered saline (PBS) solution (e.g. 0.01 M, pH 7.4) containing glucose oxidase. This enzyme-polymer mixture can then be selectively polymerized under UV light (e.g. at 365 nm, 750 mJ/cm2), for example through a Pyrex® cover using a shadow mask so that the glucose oxidase enzymes get entrapped within the locally formed layer. In certain embodiments of the invention, such PVA-SbQ entrapment appears to be superior to crosslinking methods that use glutaraldehyde as an immobilization reagent, perhaps by minimizing the reduction in glucose oxidase activity that is observed with such conventional crosslinking methods.

PVA-SbQ polymers used in embodiments of the invention are typically free from antimicrobial agents and have a neutral pH range. In typical embodiments of the invention, GOx solutions can be mixed into this photo-sensitive polymer and then exposed to UV light for a short time period so that the PVA-SbQ polymer is crosslinked in a manner that entraps GOx within the PVA-SbQ polymer matrix. In certain embodiments of the invention one can further crosslink these compositions with additional processes (e.g. a plasma deposition process) or agents (e.g. glutaraldehyde) to, for example, more strongly secure entrapped GOx molecules within the polymer matrix. Such compositions can be used to make sensors having a very stable Isig over time as well as a better linearity of sensor response. Such compositions can also be used to generate sensors having a better Isig quality in vivo due to the resultant sensor structure, i.e. ones having a hydrogel (a hydrogel which can function as an electrolyte retaining layer) in close proximity to a sensor electrode.

In typical embodiments of the invention, the amount of SbQ attached to PVA can vary from about 0.5 mol % to 10 mol %. The relative photosensitivity of PVA-SbQ increased with increasing amount of bound SbQ in the case of high molecular weight (e.g. mw 77 kd to 79 kd), and decreased with decreasing molecular weight of PVA with about constant amount of bound SbQ (1.3 mol %). For example, a higher SbQ content in the PVA-based polymer can be used to increase the cross-linked density of the resultant polymer membrane. In typical embodiments of the invention, the matrix structure is dense and stable enough to maintain its integrity over the time in aqueous medium. As one considers optimal sensor performance in a giving sensing environment, a series of parameters such as permeability to compounds such as O2 and glucose, temperature effects, O2 permeability etc. can be considered to design optimized compositions for particular applications. For example, different UV crosslinking times as well as compositions with different PVA-SbQ concentrations and/or molecular weights can be used to, for example, optimize polymer entrapment capability, to raise Isig levels, as well as to improve the temperature effect and interference rejection. In one illustrative embodiment of the invention having such selected parameters, the MW of PVA-SbQ is (MPPbioj-070) ~27 kD with 4.1% SbQ; the membrane thickness is 3-5 um; the GOx loading is 20 to 40 ku/mL within the GOx and PVA-SbQ mixture solution; and UV exposure is 1 to 3 minutes.

In certain embodiments of the invention, the electrolyte retaining layer is multifunctional and, for example functions as both an electrolyte retaining layer as well as an analyte sensing layer (e.g. one comprising glucose oxidase). Typically, such layers are at least 5, 6, 7, 8, 9 or 10 μm thick. In illustrative embodiments, this layer can comprise proteins such as BSA, HSA and GOx (e.g. one made using GOx concentrations between 10 ku to 45 ku/mL) as well as hydrophilic polymers such as PVA-SbQ and PVA-VA etc. (e.g. one made using a 5% polymer concentration and GOx concentrations between 10 ku to 55 ku/mL). As discussed below, in other embodiments of the invention, the electrolyte retaining layer can be made from a variety of materials in order to allow it to have multiple functions.

In some embodiments of the invention, an electrolyte retaining layer functions as an interference rejection membrane. Other embodiments of the invention can use a separate interference rejection membrane (e.g. in addition to an electrolyte retaining membrane) that inhibits the diffusion therethrough of compounds having a molecular weight greater than 140 Daltons. In some embodiments of the invention, the electrolyte retaining layer and/or interference rejection membrane comprises crosslinked Poly(2-hydroxyethyl methacrylate) polymers having an average molecular weight between 100 and 1000 kilodaltons. In other embodiments of the invention, the electrolyte retaining layer and/or interference rejection membrane comprises crosslinked primary amine polymers having an average molecular weight between 4 and 500 kilodaltons. In some embodiments of the invention comprising crosslinked primary amine polymers, the crosslinked primary amine polymers comprise polylysine polymers poly (allylamine) polymers; amine terminated poly(ethylene oxide) polymers; poly(vinylamine) polymers; or polyethylenimine polymers. Interference rejection membranes useful with embodiments of the invention are described, for example, in U.S. patent application Ser. No. 12/572,087, the contents of which are incorporated by reference.

Embodiments of the invention that incorporate a plasma deposition process include an amperometric analyte sensor apparatus comprising a base layer, a conductive layer disposed on the base layer and comprising a working electrode, an analyte sensing layer disposed on the working electrode. In this embodiment, the analyte sensing layer comprises an oxidoreductase such as glucose oxidase that has been entrapped within a UV crosslinked poly(vinyl alcohol)-styrylpyridinium polymer matrix. In certain embodiments of the invention, the analyte sensing layer is further modified by a plasma deposition process (see, e.g. Example 3) in order to, for example, crosslink the surface of this layer. Such plasma deposition processes can be used, for example, to enhance adhesion between layers of the sensor. Some embodiments of this invention that use this process to enhance adhesion do not utilize layers of an adhesion promoter (AP) such as APTES (3-aminopropyltriethoxysilane). In certain embodiments of the invention, the analyte sensing layer (and optionally other layers within the sensor) do not comprise a carrier protein such as human serum albumin or bovine serum albumin. In certain embodiments of the invention, the analyte sensing layer comprises glucose oxidase entrapped within a UV crosslinked poly(vinyl alcohol)-styrylpyridinium matrix which also functions as an electrolyte retaining layer and is in operable contact with the conductive layer. Typically, the electrolyte retaining layer is formed from a composition selected to absorb 10% to 50% water by weight. Typically, these sensors include one or more additional layers such as an analyte modulating layer disposed over the conductive and analyte sensing layers. A related embodiment of the invention is a composition of matter comprising glucose oxidase entrapped within a UV crosslinked poly(vinyl alcohol)-styrylpyridinium polymer matrix (e.g. one disposed over a metallic electrode), wherein this polymer matrix further comprises a surface having polymeric moieties crosslinked by a plasma deposition process.

Another embodiment of the invention is a method of making a sensor apparatus for implantation within a mammal comprising the steps of: providing a base layer; forming a conductive layer on the base layer, wherein the conductive layer includes a working electrode. In such methodological embodiments, one can then form an analyte sensing layer disposed over the conductive layer, wherein the analyte sensing layer comprises glucose oxidase UV crosslinked with a poly(vinyl alcohol)-styrylpyridinium compound. In this methodology, the GOx-PVA-SbQ layer can then be modified by a plasma deposition process (e.g. a helium plasma process, an allylamine/HDMSO pulse plasma deposition process, a HMDSO alone pulse plasma deposition or the like) so as to crosslink a surface of the GOx-PVA-SbQ layer, and for example, facilitate adhesion between layers. Such sensor embodiments include those having no glutaraldehyde (and/or byproducts from crosslinking processes using this compound), and/or no serum albumin proteins and/or no adhesion promoting materials (e.g. APTES). The methods typically further include forming one or more of the other layered elements (e.g. an analyte modulating layer) over the analyte sensing layer.

A variety of materials can be used to make analyte modulating layers having various thicknesses in embodiments of the invention. Illustrative analyte modulating layers useful with embodiments of the invention are described, for example, in U.S. patent application Ser. No. 12/643,790, the contents of which are incorporated by reference. Optionally a material used in this layer exhibits a water adsorption profile wherein the polymer absorbs 40-60% water by membrane weight. Typically, this layer is at least 3, 4, 5, 6, 7, 8, 9, 10, 11 or 12 um thick. In certain embodiments of the invention, the thickness of the analyte modulating layer is controlled in order to modulate the diffusion of molecules such as glucose through the sensor layers, for example in situations where an electrode composition may not function optimally in the presence of a high glucose flux (e.g. certain sputtered Pt electrode compositions formed from thin film processes). For example, in certain embodiments of the invention, the analyte modulating layer is 2 to 3 (e.g. 2.5, 2.6, 2.7, 2.8 etc.) times the thickness of the 3, 4, 5, 6, 7, 8, 9, 10, 11 or 12 um thick layers used with other sensor embodiments in order to modulate the ability of glucose to access and react with glucose oxidase within the sensor (e.g. glucose oxidase entrapped within a PVA-SbQ polymer matrix). Such embodiments of the invention can, for example, be use to inhibit the decay in sensor Isig that is observed over time.

Typically, the analyte modulating layer comprises a linear polyurethane/polyurea polymer. In certain embodiments, the analyte modulating layer comprises a blended mixture of a linear polyurethane/polyurea polymer and a branched acrylate polymer blended together at a ratio of between 1:1 and 1:20 by weight %. In illustrative embodiments of the invention, the analyte modulating layer comprises a blended mixture of a polyurethane/polyurea polymer formed from a mixture comprising a diisocyanate; a hydrophilic polymer comprising a hydrophilic diol or hydrophilic diamine; and a siloxane having an amino, hydroxyl or carboxylic acid functional group at a terminus; with this polyurethane/polyurea polymer blended with a branched acrylate polymer formed from a mixture comprising a butyl, propyl, ethyl or methylacrylate; an amino-acrylate; a siloxane-acrylate; and a poly (ethylene oxide)-acrylate. In certain embodiments of the invention, the analyte modulating layer exhibits a permeability to glucose that changes less than 2% per degree centigrade over a temperature range of 22 to 40 degrees centigrade. Optionally the analyte modulating layer exhibits a water adsorption profile of 40-60% of membrane weight. Typically the analyte modulating layer is 5-12 um thick.

As disclosed herein, certain combinations of the elements disclosed herein generate amperometric sensors having unexpected characteristics including a low background current, a relatively high sensitivity, low interference responses and low system noise levels. In particular sensors having a combination of a sputtered platinum electrode composition and a layer of material comprising crosslinked Poly(2-hydroxyethyl methacrylate) polymers having an average molecular weight between 100 and 1000 kilodaltons; or crosslinked primary amine polymers having an average molecular weight between 4 and 500 kilodaltons exhibit these highly desirable properties. In addition, when these elements are further combined with an modulating layer comprises a blended mixture of a linear polyurethane/polyurea polymer and a branched acrylate polymer blended together at a ratio of between 1:1 and 1:20 by weight %, the sensors exhibit further desirable qualities, for example a permeability to glucose that changes less than 2% per degree centigrade over a temperature range of 22 to 40 degrees centigrade.

As disclosed herein, embodiments of the invention can include a number of other layered elements. In certain embodiments of the invention, the sensor apparatus further comprises at least one of a protein layer disposed over the analyte sensing layer; an adhesion promoting layer disposed over the analyte sensing layer, wherein the adhesion promoting layer promotes the adhesion between the analyte sensing layer and an adjacent layer; or a cover layer disposed over the analyte sensor apparatus, wherein the cover layer comprises an aperture positioned on the cover layer so as to facilitate an analyte present in the mammal contacting and diffusing through an analyte modulating layer; and contacting the analyte sensing layer. In typical embodiments of the invention, the analyte sensor apparatus is formed from biocompatible materials and exhibits an architecture compatible with implantation within a mammal.

A related embodiment of the invention is a method of making a sensor apparatus for implantation within a mammal comprising the steps of: providing a base layer; forming a conductive layer on the base layer, wherein the conductive layer includes a working electrode formed from a sputtered platinum composition; forming an electrolyte retaining layer in operable contact with the conductive layer, wherein the electrolyte retaining layer is formed from a composition selected to absorb 10% to 50% water by weight; forming an analyte sensing layer disposed over the conductive layer; and forming an analyte modulating layer disposed over the analyte sensing layer. In some embodiments of the invention, the sputtered platinum composition is formed to exhibit a root-mean-square roughness value below 3 nanometers. Optionally in such methods, the electrolyte retaining layer is formed to function as an interference rejection membrane that inhibits the diffusion therethrough of compounds having a molecular weight greater than 140 Daltons.

As noted above, certain embodiments of these methods further comprise forming an interference rejection membrane on the working electrode. Interference rejection membranes useful with embodiments of the invention are described, for example, in U.S. patent application Ser. No. 12/572,087, the contents of which are incorporated by reference. Typically, the interference rejection membrane comprises crosslinked methacrylate polymers or crosslinked primary amine polymers; and/or forming the analyte sensing layer to include an oxidoreductase; forming a protein layer on the analyte sensing layer forming an adhesion promoting layer on the analyte sensing layer or the optional protein layer; and/or forming a cover layer disposed on at least a portion of the analyte modulating layer, wherein the cover layer further includes an aperture over at least a portion of the analyte modulating layer. In certain embodiments of the invention, the crosslinked methacrylate polymers comprise Poly(2-hydroxyethyl methacrylate) (pHEMA) polymers having an average molecular weight of between 100 and 1000 kilodaltons. Typically the polymers are crosslinked by a hydrophilic crosslinking agent.

In some embodiments of the invention, the analyte modulating layer is formed to comprise a blended mixture of a linear polyurethane/polyurea polymer and a branched acrylate polymer such as those disclosed in U.S. patent application Ser. No. 12/643,790, the contents of which are incorporated by reference. Typically these polymers are blended together at a ratio of between 1:1 and 1:20 by weight %, with the polyurethane/polyurea polymer being formed from a mixture comprising a diisocyanate; a hydrophilic polymer comprising a hydrophilic diol or hydrophilic diamine; and a siloxane having an amino, hydroxyl or carboxylic acid functional group at a terminus; and the branched acrylate polymer formed from a mixture comprising a butyl, propyl, ethyl or methyl-acrylate; an amino-acrylate; a siloxane-acrylate; and a poly(ethylene oxide)-acrylate. Typically the analyte modulating layer is formed to exhibit a permeability to glucose that changes less than 2% per degree centigrade over a temperature range of 22 to 40 degrees centigrade.

A specific illustrative example of a sensor embodiment of the invention comprises a base polyimide, patterned metal traces, and insulation polyimide all positioned on top of a glass plate. In this embodiment, the metal sputtering process is a subsequent step in this stage of the substrate building process. Metals can be applied to the surface of the base polyimide to be formed into the conductors, electrodes, and contact pads of the sensor in the next step in the process. The method used to transfer one or more metals from the source to the substrate is typically a sputter deposition process. As is known in the art, sputter deposition is a physical vapor deposition (PVD) method of depositing thin films by sputtering, that is ejecting, material from a "target," that is source, which then deposits onto a "substrate," such as a silicon wafer. Sputtering sources are usually magnetrons that utilize strong electric and magnetic fields to trap electrons close to the surface of the magnetron, which is known as the target. The electrons follow helical paths around the magnetic field lines undergoing more ionizing collisions with gaseous neutrals near the target surface than would otherwise occur. The sputter gas is inert, typically argon. Illustrative sputtering processes known in the art include, for example, ion-beam sputtering, reactive sputtering, ion-assisted deposition, high-target-utilization sputtering, and gas flow sputtering. Illustrative methods and materials for such processes are described, for example, in U.S. Pat. Nos. 5,282,946, 7,229, 588 4,253,931, 4,400,255, and in HANDBOOK OF ION SOURCES Bernhard Wolf Ed. (1995) CRC Press.

In an exemplary embodiment of a sputter process, chrome is applied first to act as an adhesion or seed layer. Gold is then applied to act as the main conductor of the sensor. Optionally the Cr layer is replaced by Titanium and Au by Platinum for different applications. The thicknesses of each layer can be decided by factors such as mechanical properties and/or the requirements for subsequence process steps (e.g. etching and/or electroplating). A Pt application of less than 1 k Angstrom thick on top of either Cr or Ti (seed layer) and Au (primary conductor) can done, for example, at 0.4 kW, ~6.0 mTorr, & 138 Angstrom/min.

Yet another embodiment of the invention is a composition of matter comprising a sputtered platinum composition; and a hydrophilic polymer composition comprising crosslinked Poly(2-hydroxyethyl methacrylate) polymers having an average molecular weight between 100 and 1000 kilodaltons; or crosslinked primary amine polymers having an average molecular weight between 4 and 500 kilodaltons. Optionally the composition of matter further comprises a blended mixture of a linear polyurethane/polyurea polymer and a branched acrylate polymer blended together at a ratio of between 1:1 and 1:20 by weight %.

Figure 2A:
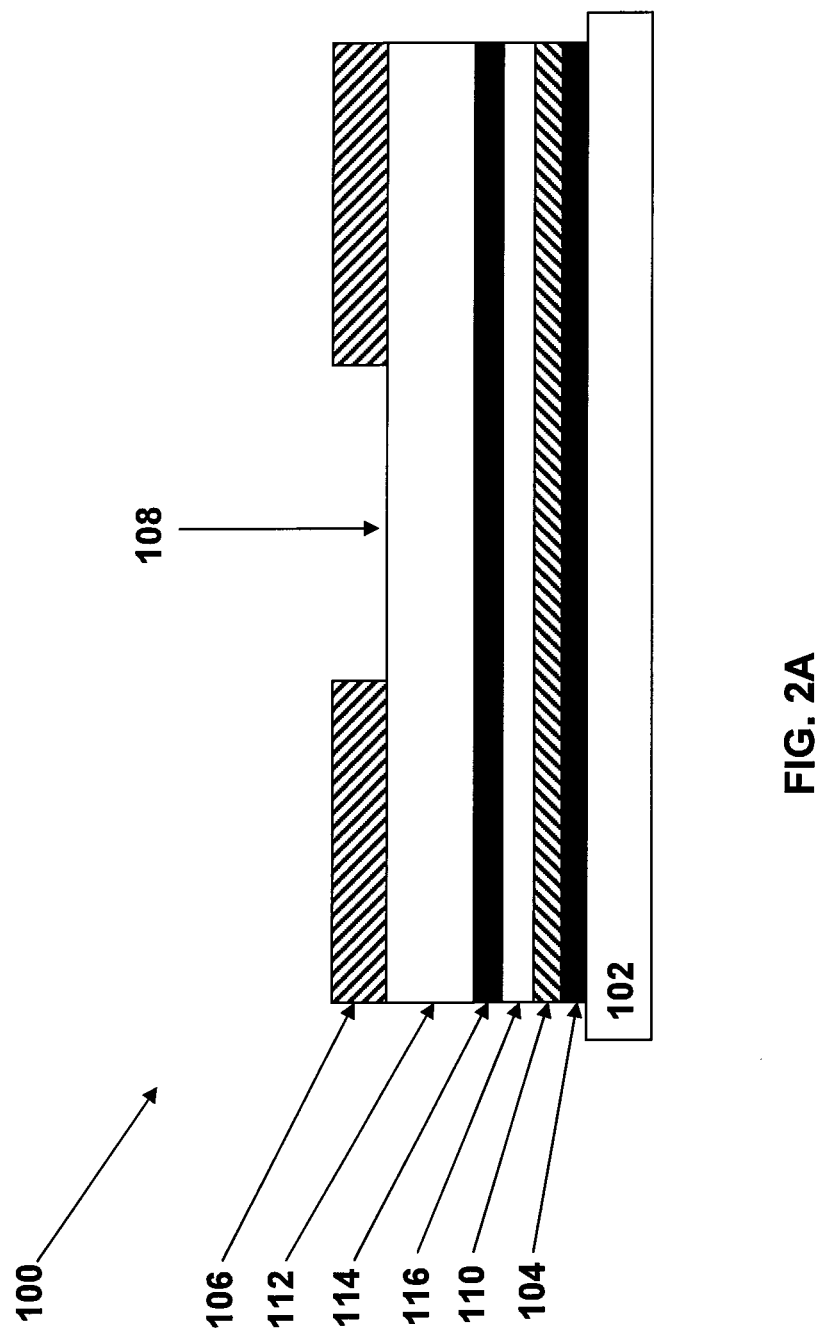
FIG. 2A provides a diagrammatic view of one embodiment of an amperometric analyte sensor having a plurality of layered compositions.
Figure 2B:
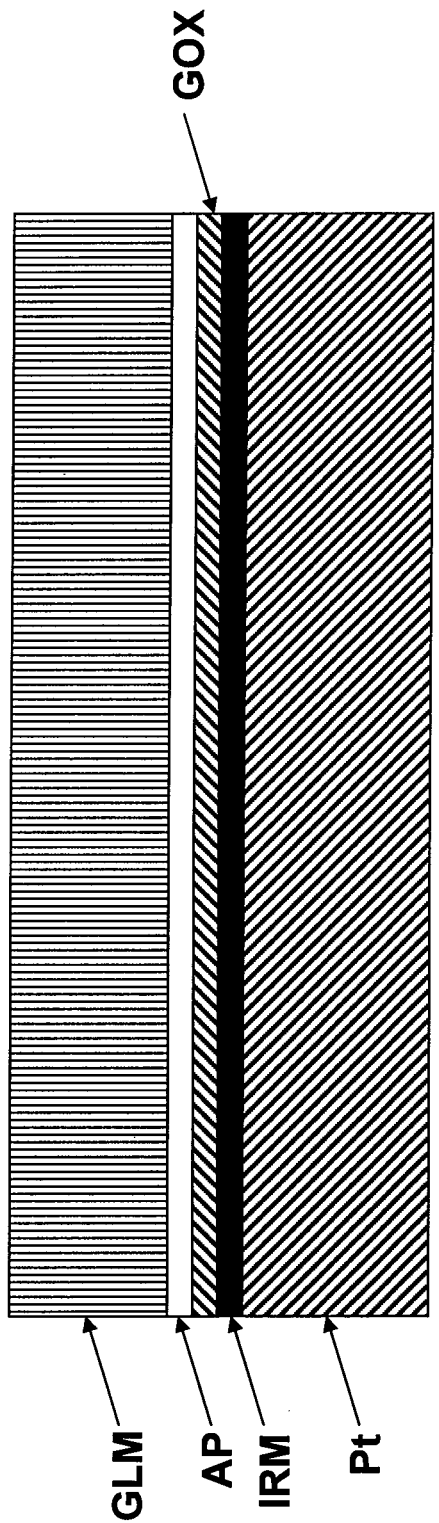
FIG. 2B provides a diagrammatic view of embodiments of an amperometric analyte sensor having an arrangement of layers comprising, from the bottom to the top of the figure, an electrode made from a sputtered platinum composition, a layer comprising an interference rejection membrane (IRM), an analyte sensing layer comprising GOx, a layer comprising an adhesion promoting (AP) composition, and a glucose limiting membrane (GLM).

In some sensor embodiments, an adhesion promoter layer is added to facilitate close attachment of various layers such as a diffusion control membrane and enzyme layer. One such sensor embodiment is shown in FIG. 2A. Alternatively some sensor embodiments do not include any adhesion promoter layer(s). Typical embodiments of the invention disclosed herein include an interference rejection membrane that is designed to inhibit and/or prevent endogenous or exogenous electro-active substances in vivo (e.g. in interstitial fluid) such as acetaminophen, uric acid and ascorbic acid from accessing the sensor electrode and being oxidized at the electrode surface (and consequently produce a spurious signal that can confound measurements of the signal generated by the analyte to be measured). One embodiment of a sensor having an interference rejection membrane is shown in FIG. 2B.

One example of an IRM useful in embodiments of the invention comprises a polymeric composition comprising methacrylate polymers having a molecular weight between 100 and 1000 kilodaltons, wherein the methacrylate polymers are crosslinked by a hydrophilic crosslinking agent such as an organofunctional dipodal alkoxysilane. Another IRM embodiment of the invention is a polymeric composition comprising primary amine polymers having a molecular weight between 4,000 Daltons and 500 kilodaltons, wherein the primary amine polymers are crosslinked by a hydrophilic crosslinking agent such as glutaraldehyde. Typically these crosslinked polymeric IRM compositions coat sputtered platinum composition. In an illustrative embodiment, the platinum composition comprises an electrode; and the crosslinked polymeric composition is coated on the electrode in a layer between 0.1 μm and 1.0 μm thick. A related embodiment of the invention is a composition comprising an electrode (e.g. a sputtered platinum electrode used in an amperometric sensor) having an electroactive surface coated with, and in direct contact with a layer of crosslinked methacrylate polymers or crosslinked primary amine polymers. In certain embodiments of the invention, the IRM is designed to function (i.e. inhibit the diffusion of an interferent) where the molecular weight of the interferent is at least 140 Daltons. Typically, the IRM inhibits the diffusion of acetaminophen, ascorbic acid and/or uric acid there through to the electroactive surface of an electrode within an analyte sensor.

In certain embodiments of the invention, the IRM layer of polymers is disposed on a sputtered platinum working electrode of an amperometric sensor and is crosslinked by a hydrophilic crosslinking agent that facilitates the hydration of the layer. A number of different hydrophilic crosslinking compounds useful to couple either methacrylate polymers or polyamine polymers are known in the art. Illustrative crosslinking compounds include for example, glutaraldehyde, urea; an ethylene glycol dimethacrylate; a polyethylene glycol diacrylate; an organofunctional dipodal alkoxysilane or the like. Typically, methacrylate (e.g. 2-hydroxyethyl methacrylate) polymers are crosslinked with a hydrophilic crosslinking agent that reacts with hydroxyl moieties such as an alkoxysilane crosslinker. Typically, primary amine (e.g. polylysine) polymers are crosslinked with a hydrophilic crosslinking agent that reacts with primary amine moieties such as glutaraldehyde. Suitable primary amine polymers include polylysine, poly(allylamine), Poly(ethylene oxide), diamine terminated, Poly(vinylamine), branched Polyethylenimine and Jeffamine Series primary amine-based oligomer or polymers etc. (and their salts). One typical compound used to make polyamine IRMs is polylysine hydrobromide having a MW of 50 kd to 500 kd.

Another illustrative embodiment of the invention is an amperometric analyte sensor apparatus (e.g. one designed for implantation within a mammal) comprising: a base layer; a conductive layer disposed on the base layer and comprising a sputtered platinum working electrode; an electrolyte maintaining layer and/or interference rejection membrane disposed on an electroactive surface of the working electrode, wherein the electrolyte maintaining layer and/or interference rejection membrane comprises polymers crosslinked by a hydrophilic crosslinking agent; and an analyte sensing layer (e.g. one in direct contact with the interference rejection membrane). The electrolyte maintaining layer and/or interference rejection membrane in this embodiment can comprise crosslinked primary amine or crosslinked methacrylate (e.g. Poly(2-hydroxyethyl methacrylate) polymers. The crosslinked methacrylate polymers in this membrane are typically crosslinked by a hydrophilic crosslinking agent (e.g. a urea; an ethylene glycol dimethacrylate; a polyethylene glycol diacrylate; an organofunctional alkoxysilane or the like) so that the hydrophilicity of the interference rejection membrane is increased. Desirable methacrylate crosslinking agents include compounds such as organo-functional alkoxysilanes that react with organic polymers to attach the trialkoxysilyl group onto the polymer backbone. In such reactions, the silane is then available to react with moisture to crosslink the silane into a stable three-dimensional silane structure. Such mechanisms can be used to crosslink plastics, especially polyethylene, and other organic resins, such as acrylics and urethanes to impart the durability, heat resistance to coatings. In addition, crosslinkers such as a hydrophilic dipodal silane gives a double strength of crosslinking capacity while concurrently offering excellent hydrophilicity.

Certain crosslinked polymer compositions disclosed herein allow the design of extremely thin interference rejection membranes that do not substantially increase the thickness of an existing sensor structure. Typically the interference rejection membranes are between 0.1 to 1.0 µm thick (e.g. between 0.1 and 0.2, 0.3, 0.4, 0.5, 0.6, 0.7, 0.8, 0.9 or 1.0 thick), a thickness that allows them to be readily adapted for use with a variety of existing sensor designs without making substantial changes to these designs to accommodate this additional element. In preferred embodiments, the interference rejection membranes are between 0.1-0.2 µm thick. These thin interference rejection membranes can be used for example in implantable sensor embodiments of the invention to facilitate hydration of a sensor, as well as to inhibit the diffusion rate of compounds such as acetaminophen, ascorbic acid and uric acid therethrough while not substantially increasing the bulk of the implanted device (thereby decreasing the likelihood of a patient experiencing complications associated with implantation of the device). Optionally the interference rejection membranes inhibit the diffusion of acetaminophen therethrough in a manner that decreases a signal in the analyte sensor apparatus that results from a concentration of acetaminophen by at least 50% as compared to a control analyte sensor apparatus lacking the interference rejection membrane.

Embodiments of the invention include a wide variety of sensor elements and configurations of elements. For example, in certain embodiments of the invention, the electrolyte maintaining layer and/or interference rejection membrane is in direct contact with an electrochemically reactive surface of the sputtered platinum working electrode; and the analyte sensing layer is disposed on the interference rejection membrane. In some embodiments of the invention, the electrolyte maintaining layer and/or interference rejection membrane comprises a plurality of coatings of the polymeric material (e.g. coatings disposed on a sputtered platinum electrode via a spray process as disclosed in the Examples below). Typically the analyte sensing layer comprises an oxidoreductase (e.g. glucose oxidase) that generates hydrogen peroxide upon exposure to a substrate for the oxidoreductase (e.g. glucose), wherein the amount of hydrogen peroxide generated by the oxidoreductase is proportional to the amount of substrate exposed to the oxidoreductase. Optionally such embodiments of the invention further include: a protein layer disposed on the analyte sensing layer; an analyte modulating layer disposed on the analyte sensing layer or the protein layer, wherein the analyte modulating layer comprises a composition that modulates the diffusion of an analyte such as glucose diffusing through the analyte modulating layer; an optional adhesion promoting layer disposed on the analyte sensing layer, wherein the adhesion promoting layer promotes the adhesion between the analyte sensing layer and an analyte modulating layer; or a cover layer disposed on the analyte sensor apparatus, wherein the cover layer comprises an aperture positioned on the cover layer so as to facilitate an analyte present in the mammal accessing and diffusing through an analyte modulating layer; and accessing the analyte sensing layer. In some embodiments of the invention, the conductive layer comprises a plurality of electrodes including the working electrode, a counter electrode and a reference electrode. Optionally, one or more proteins in the layers is entrapped or crosslinked within a layer.

Optionally the conductive layer comprises a plurality of sputtered platinum working electrodes, counter electrodes and reference electrodes; and the plurality of working, counter and reference electrodes are grouped together as a unit and positionally distributed on the conductive layer in a repeating pattern of units. In some embodiments of the invention, the sensor is operatively coupled to: a sensor input capable of receiving a signal from the sensor that is based on a sensed physiological characteristic value in the mammal; and a processor coupled to the sensor input, wherein the processor is capable of characterizing one or more signals received from the sensor. In certain embodiments of the invention, a pulsed voltage is used to obtain a signal from an electrode.

Another embodiment of the invention is a method of making a sensor apparatus for implantation within a mammal comprising the steps of: providing a base layer; forming a conductive layer on the base layer, wherein the conductive layer includes a sputtered platinum working electrode; forming an interference rejection membrane on the working electrode, wherein the interference rejection membrane functions as an electrolyte maintaining layer and comprises crosslinked methacrylate polymers or crosslinked primary amine polymers; forming an analyte sensing layer on the conductive layer, wherein the analyte sensing layer includes an oxidoreductase; optionally forming a protein layer on the analyte sensing layer; optionally forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. Yet another embodiment of the invention is a method of sensing analyte using sensors having the disclosed constellation of elements and/or made by the disclosed methodological steps.

As noted above, embodiments of the invention include analyte modulating layers made from blended polymer compositions. As is known in the art, a polymer comprises a long or larger molecule consisting of a chain or network of many repeating units, formed by chemically bonding together many identical or similar small molecules called monomers. A copolymer or heteropolymer is a polymer derived from two (or more) monomeric species, as opposed to a homopolymer where only one monomer is used. Copolymers may also be described in terms of the existence of or arrangement of branches in the polymer structure. Linear copolymers consist of a single main chain whereas branched copolymers consist of a single main chain with one or more polymeric side chains. Sensor membranes made from blended polymeric compositions disclosed herein can optimize analyte sensor function including sensor sensitivity, stability and hydration profiles. In addition, by optimizing the stoichiometry of reactant species over a range of sensor temperatures, the membranes disclosed herein can optimize the chemical reactions that produce the critical measurable signals that correlate with the levels of an analyte of interest (e.g. glucose). The following sections describe illustrative sensor elements, sensor configurations and methodological embodiments of the invention.

One polymeric composition used in analyte modulating layer embodiments of the present invention is a polyurethane/polyurea polymer. As used herein, the term "polyurethane/polyurea polymer" refers to a polymer containing urethane linkages, urea linkages or combinations thereof. As is known in the art, polyurethane is a polymer consisting of a chain of organic units joined by urethane (carbamate) links. Polyurethane polymers are typically formed through step-growth polymerization by reacting a monomer containing at least two isocyanate functional groups with another monomer containing at least two hydroxyl (alcohol) groups in the presence of a catalyst. Polyurea polymers are derived from the reaction product of an isocyanate component and a diamine. Typically, such polymers are formed by combining diisocyanates with alcohols and/or amines. For example, combining isophorone diisocyanate with PEG 600 and aminopropyl polysiloxane under polymerizing conditions provides a polyurethane/polyurea composition having both urethane (carbamate) linkages and urea linkages. Such polymers are well known in the art and described for example in U.S. Pat. Nos. 5,777,060, 5,882,494 and 6,632,015, and PCT publications WO 96/30431; WO 96/18115; WO 98/13685; and WO 98/17995, the contents of each of which is incorporated by reference.

Another embodiment of the invention is an amperometric analyte sensor apparatus comprising: a base layer; a conductive layer disposed on the base layer and comprising a sputtered platinum working electrode; an analyte sensing layer disposed on the conductive layer (e.g. one comprising an oxidoreductase such as glucose oxidase); and an analyte modulating layer disposed on the analyte sensing layer. In this embodiment of the invention, the analyte modulating layer comprises a blended mixture of a linear polyurethane/polyurea polymer, and a branched acrylate polymer; with these polymers blended at a ratio of at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20 by weight %. Typically in such embodiments, the linear polyurethane/polyurea polymer used to make homogeneous blended polymeric compositions that exhibit a permeability to glucose that decreases by between 1% and 8% per degree centigrade as temperature is increased from 22 to 40 degrees centigrade; and the branched acrylate polymer used to make the blended polymeric composition exhibits a permeability to glucose that increases by between 1% and 8% per degree centigrade as temperature is increased from 22 to 40 degrees centigrade. Typically the polymeric composition that results from blending the linear polyurethane/polyurea with the branched acrylate polymer exhibits a permeability to glucose that changes less than 2% per degree centigrade over a temperature range of 22 to 40 degrees centigrade.

Embodiments of the invention blend polymers having opposite yet complementary glucose diffusion profiles to generate an analyte modulating composition having a stabilized glucose diffusion profile. Specifically, certain polyurea and/or polyurethane analyte modulating compositions (e.g. those disclosed in U.S. Pat. Nos. 5,777,060, 5,882,494 and 6,642,015) have a glucose diffusion profile that decreases as the temperature increases. These linear polyurea and polyurethane polymers can exhibit about a −3% per degree C. in glucose signal change from 22 to 40 degrees centigrade (i.e. the signal observed from a given concentration of glucose decreases about 3% per degree C. as temperature is increased from 22 to 40 degrees centigrade). In contrast, the branched acrylate polymers disclosed herein have a glucose diffusion profile that decreases as the temperature increases. These branched acrylate polymers exhibit about a +3% per degree C. in glucose signal change from 22 to 40 degrees centigrade (i.e. the signal observed from a given concentration of glucose increases about 3% per degree C. as temperature is increased from 22 to 40 degrees centigrade). When the linear polyurethane/polyurea polymer and the branched acrylate polymer are blended together however, the opposite temperature effects are cancelled out with the result that the blended membrane becomes an essentially non-temperature dependent glucose limiting polymer from 22 to 40 degrees centigrade.

By modulating the relative amounts of the linear polyurea/polyurethane and the branched acrylate polymers in a blend, one can ameliorate temperature dependent glucose permeability profiles that are observed with certain polymer matrices. Due to the interactions between two different polymers, the blend ratio is not necessarily the theoretical ratio of 1:1 and has been determined empirically to be between 1:1 and 1:20 by weight In this context, either polymer can be in excess and "1:20" therefore encompasses blends where the branched acrylate is present in a ½0th fraction (0.05) as well as blends where the linear polyurea/polyurethane is present in a ½0th fraction. In situations where it is desirable a glucose sensor generate a relatively low signal in response to glucose, the linear polyurea/polyurethane and the branched acrylate can be blended together at a ratio where the linear polyurea/polyurethane is in excess, such as a 2:1 ratio. In situations where it is desirable that the sensor generate a relatively high signal in response to glucose, the linear polyurea/polyurethane and the branched acrylate can be blended together at a ratio where the branched acrylate is in excess, such as a 1:2 ratio. Altering these polymer ratios can also have benefits in other contexts. For example, an increased relative amount of branched acrylate polymer in the polymer blend can enhance the adhesion between blended polymer membrane and a proximal material or layer in a sensor (e.g. a GOx layer).

Embodiments of the invention include analyte sensor apparatus having an architecture adapted to be compatible with biological tissue as well as elements made from biocompatible materials so as to be implantable in vivo. In such embodiments of the invention, a homogeneously blended polymeric composition of the analyte modulating layer facilitates in vivo hydration of the sensor so that levels of an in vivo analyte can be sensed less than 45 minutes or less than 30 minutes (including a 20 min initialization process) after sensor implantation into an in vivo environment. In addition, in certain embodiments of the invention, the blended polymeric composition of the analyte modulating layer facilitates adhesion of the layers of the sensors so as to eliminate the need for a separate layer of an adhesion promoting material between various layers of the sensor (e.g. one disposed between the analyte sensing layer and the analyte modulating layer). Optionally, the sensors of the invention further include at least one of: a protein layer disposed on the analyte sensing layer; or a cover layer disposed on the analyte sensor apparatus, wherein the cover layer comprises an aperture positioned on the cover layer so as to facilitate an analyte present in an in vivo environment from contacting and diffusing through an analyte modulating layer; and contacting the analyte sensing layer.

Embodiments of the invention include both materials (e.g. blended polymeric compositions) as well as architectures that designed to facilitate sensor performance. For example, in certain embodiments of the invention, the conductive layer comprises a plurality of sputtered platinum working electrodes and/or counter electrodes and/or reference electrodes (e.g. 3 working electrodes, a reference electrode and a counter electrode), in order to, for example, avoid problems associated with poor sensor hydration and/or provide redundant sensing capabilities. Optionally, the plurality of working, counter and reference electrodes are configured together as a unit and positionally distributed on the conductive layer in a repeating pattern of units. In certain embodiments of the invention, the base layer is made from a flexible material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment. Typically, the sensor is operatively coupled to a sensor input capable of receiving a signal from the sensor that is based on a sensed analyte; and a processor coupled to the sensor input, wherein the processor is capable of characterizing one or more signals received from the sensor. In some embodiments of the invention, a pulsed voltage is used to obtain a signal from one or more electrodes of a sensor.

The sensors disclosed herein can be made from a wide variety of materials known in the art. In one illustrative embodiment of the invention, the analyte modulating layer comprises a polyurethane/polyurea polymer formed from a mixture comprising: a diisocyanate; a hydrophilic polymer comprising a hydrophilic diol or hydrophilic diamine; and a siloxane having an amino, hydroxyl or carboxylic acid functional group at a terminus; with this polymer then blended with a branched acrylate polymer formed from a mixture comprising: a butyl, propyl, ethyl or methyl-acrylate; an amino-acrylate; a siloxane-acrylate; and a poly(ethylene oxide)-acrylate. Optionally, additional materials can be included in these polymeric blends. For example, certain embodiments of the branched acrylate polymer are formed from a reaction mixture that includes a hydroxyl-acrylate compound (e.g. 2-hydroxyethyl methacrylate).

In a specific embodiment of the invention, the analyte modulating layer comprises a polyurethane/polyurea polymer formed from a mixture comprising a diisocyanate; a hydrophilic polymer comprising a hydrophilic diol or hydrophilic diamine; and a siloxane having an amino, hydroxyl or carboxylic acid functional group at a terminus, with this polyurethane/polyurea polymer being blended with a branched acrylate polymer formed from a mixture comprising a methyl methacrylate; a 2-(dimethylamino)ethyl methacrylate; a polydimethyl siloxane monomethacryloxypropyl; a poly(ethylene oxide) methyl ether methacrylate; and a 2-hydroxyethyl methacrylate. Typically, the first polymer is formed from a mixture comprising: a diisocyanate compound (typically about 50 mol % of the reactants in the mixture); at least one hydrophilic diol or hydrophilic diamine compound (typically about 17 to 45 mol % of the reactants in the mixture); and a siloxane compound. Optionally the first polyurethane/polyurea polymer comprises 45-55 mol % (e.g. 50 mol %) of a diisocyanate (e.g. 4,4'-diisocyanate), 10-20 (e.g. 12.5 mol %) mol % of a siloxane (e.g. polymethylhydrosiloxane, trimethylsilyl terminated), and 30-45 mol % (e.g. 37.5 mol %) of a hydrophilic diol or hydrophilic diamine compound (e.g. polypropylene glycol diamine having an average molecular weight of 600 Daltons, Jeffamine 600). This first polyurethane/polyurea polymer is blended with a second polymer formed from a mixture comprising: 5-45 weight % of a 2-(dimethylamino)ethyl methacrylate compound; 15-55 weight % of a methyl methacrylate compound; 15-55 weight % of a polydimethyl siloxane monomethacryloxypropyl compound; 5-35 weight % of a poly(ethylene oxide) methyl ether methacrylate compound; and 1-20 weight % 2-hydroxyethyl methacrylate, with the first polymer and the second polymer blended together at a ratio between 1:1 and 1:20 weight %.

Sensors Comprising Multiple Layers of Oxidoreductases

As is known in the art, in typical amperometric glucose sensors, glucose oxidase is used to catalyze the reaction between glucose and oxygen to yield gluconic acid and hydrogen peroxide ($H_2O_2$). The $H_2O_2$ then reacts electrochemically with a electrode within an electrical circuit of the sensor, so that the resultant alterations in circuit current can be measured (e.g. by a potentiostat). At the same time however, this $H_2O_2$ can react with and damage the glucose oxidase enzyme, a phenomena which can reduce aspects of sensor performance and/or shorten sensor lifetimes. Consequently, there is a need in this technology for methods and materials that allow oxidoreductase (e.g. glucose oxidase) based sensors to generate an $H_2O_2$ signal at a sensor electrode that is sufficient to quantify associated glucose levels while at the same time minimizes $H_2O_2$ damage to the oxidoreductase. Embodiments of the invention that comprise glucose sensors having a plurality of glucose oxidase containing layers having different concentrations of glucose oxidase address this and other needs in this technology.

Figure 8A:
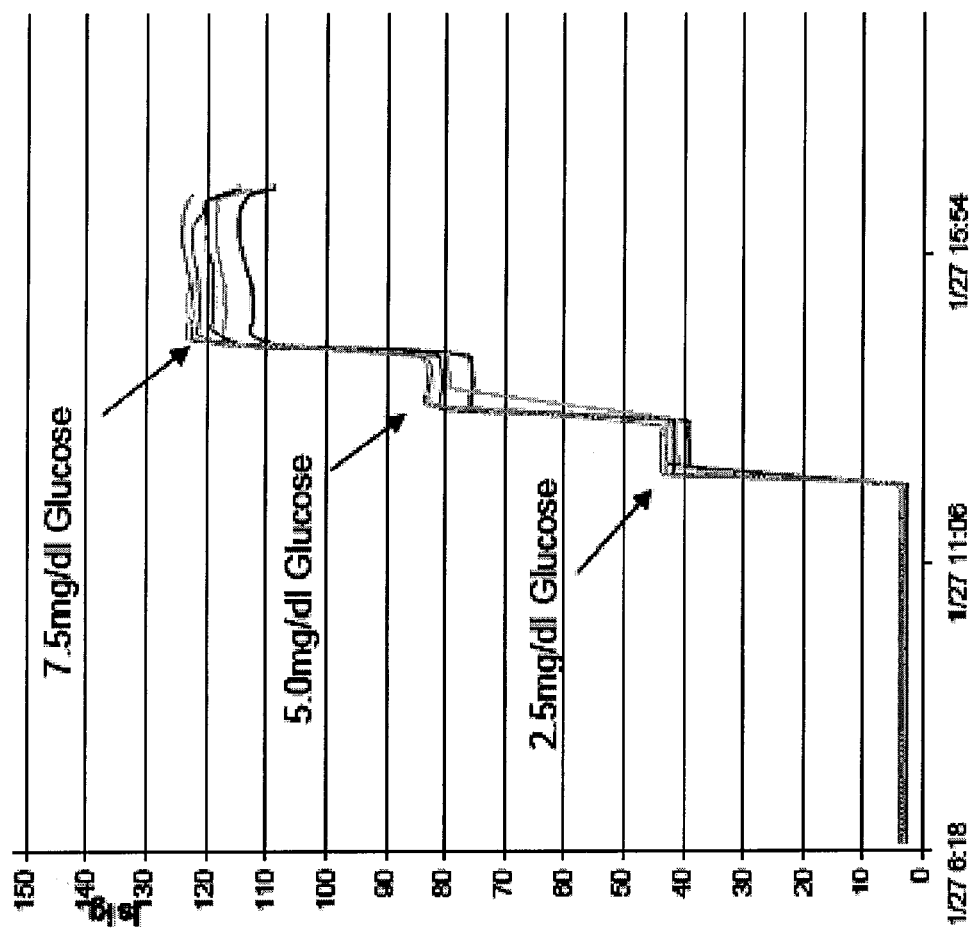
FIGS. 8A-8D provide data including data from modeling studies (e.g. those using COMSOL Multiphysics® 3.5a software) that compare performance aspects of sensors comprising glucose oxidase (GOx) compositions having a plurality of layers of GOx at the same (e.g. 45 KU-45 KU-45 KU) or different (e.g. 5 KU-45 KU-45 KU) concentrations. In the graphs shown in 8B-8C, "45 KU-45 KU-45 KU" for example, represents a composition formed from three layers of glucose oxidase having a concentration of 45 KU/mL; while "5 KU-45 KU-45 KU" represents a composition formed from three layers of glucose oxidase having respective concentrations of 5 KU/mL, 45 KU/mL and 45 KU/mL, and "45 KU" represents a composition formed from a single layer of glucose oxidase having a concentration of 45 KU/mL. In these graphs, the right-most concentration layer (e.g. 45 KU) represents the layer that is proximal to the electrode surface.
Figure 8B:
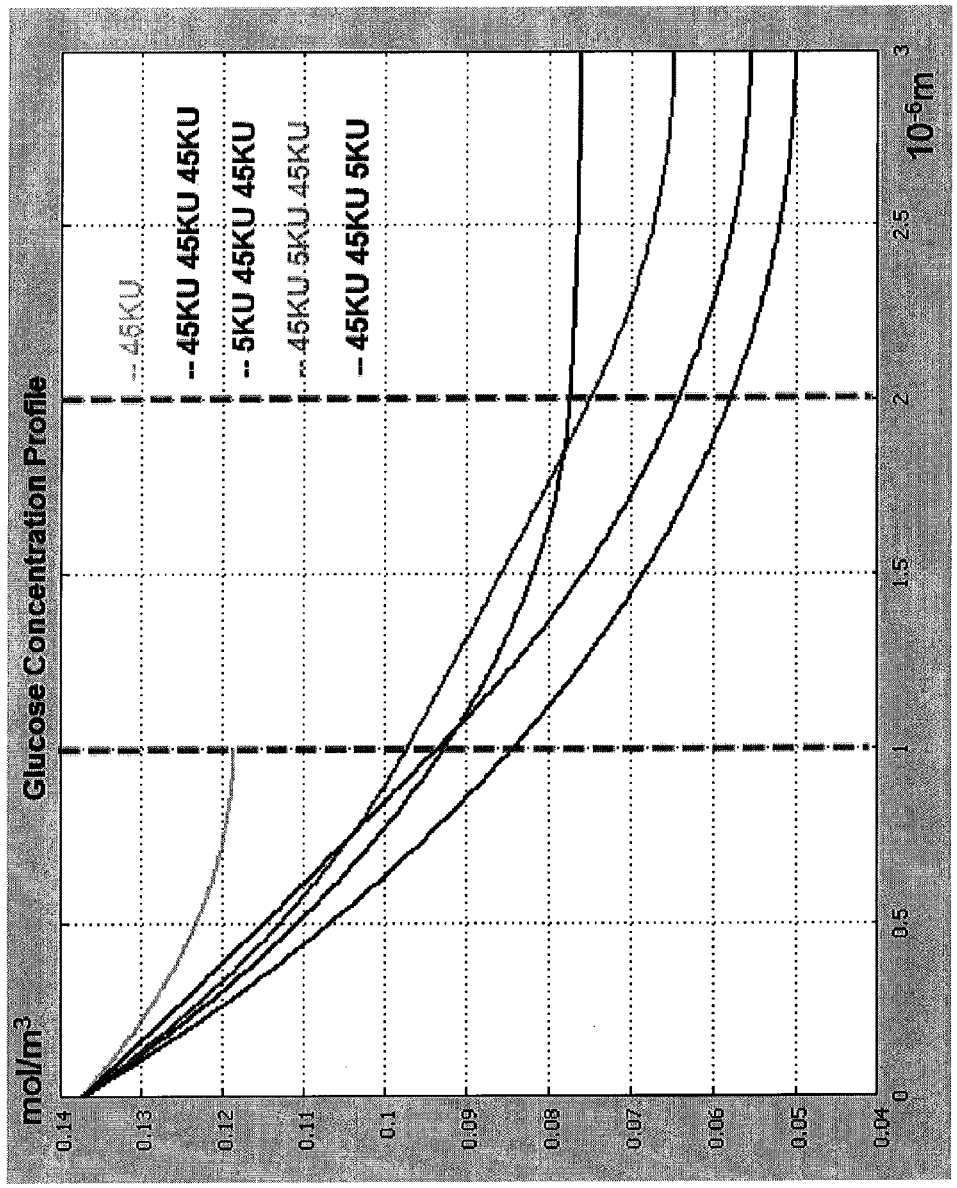
Figure 8C:
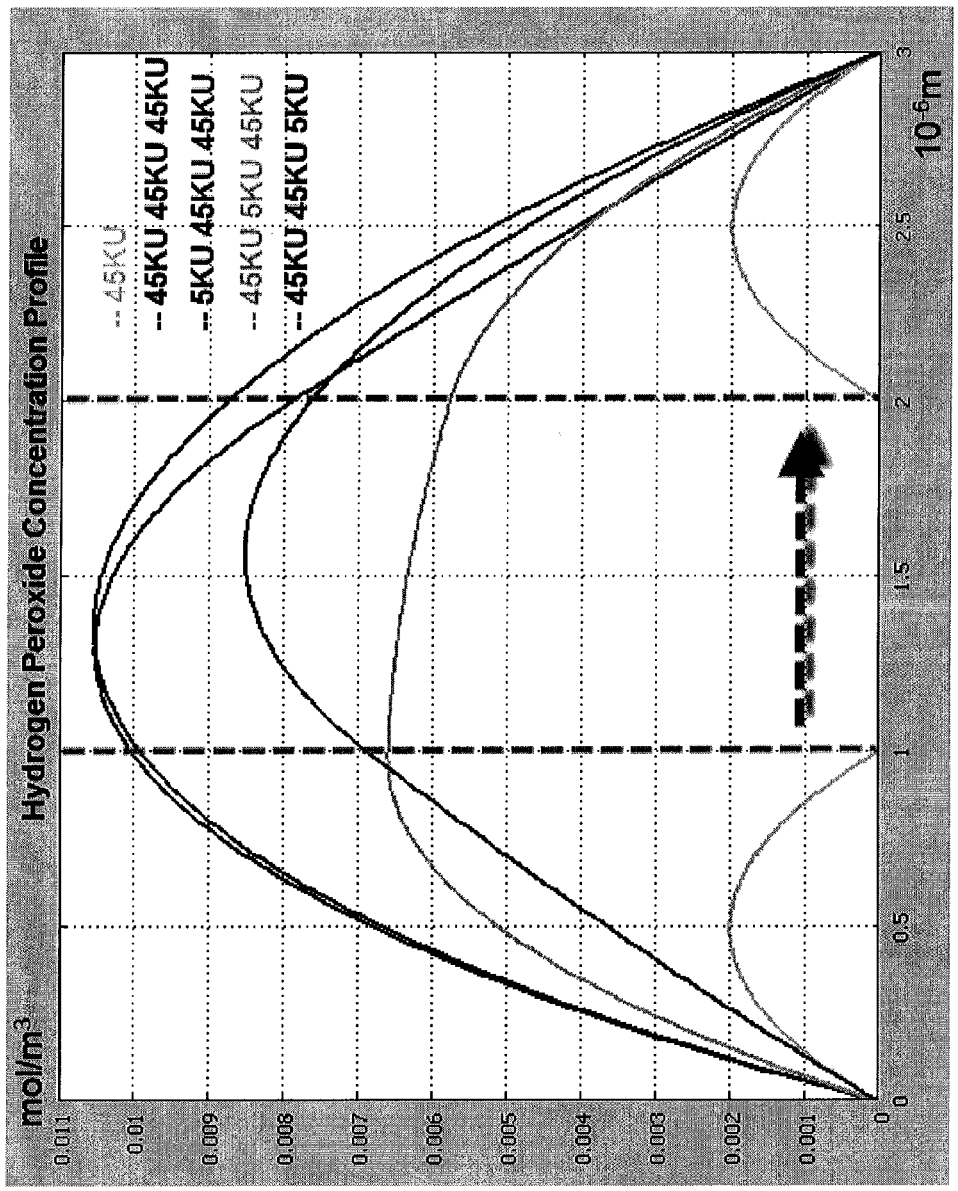
Figure 8D:
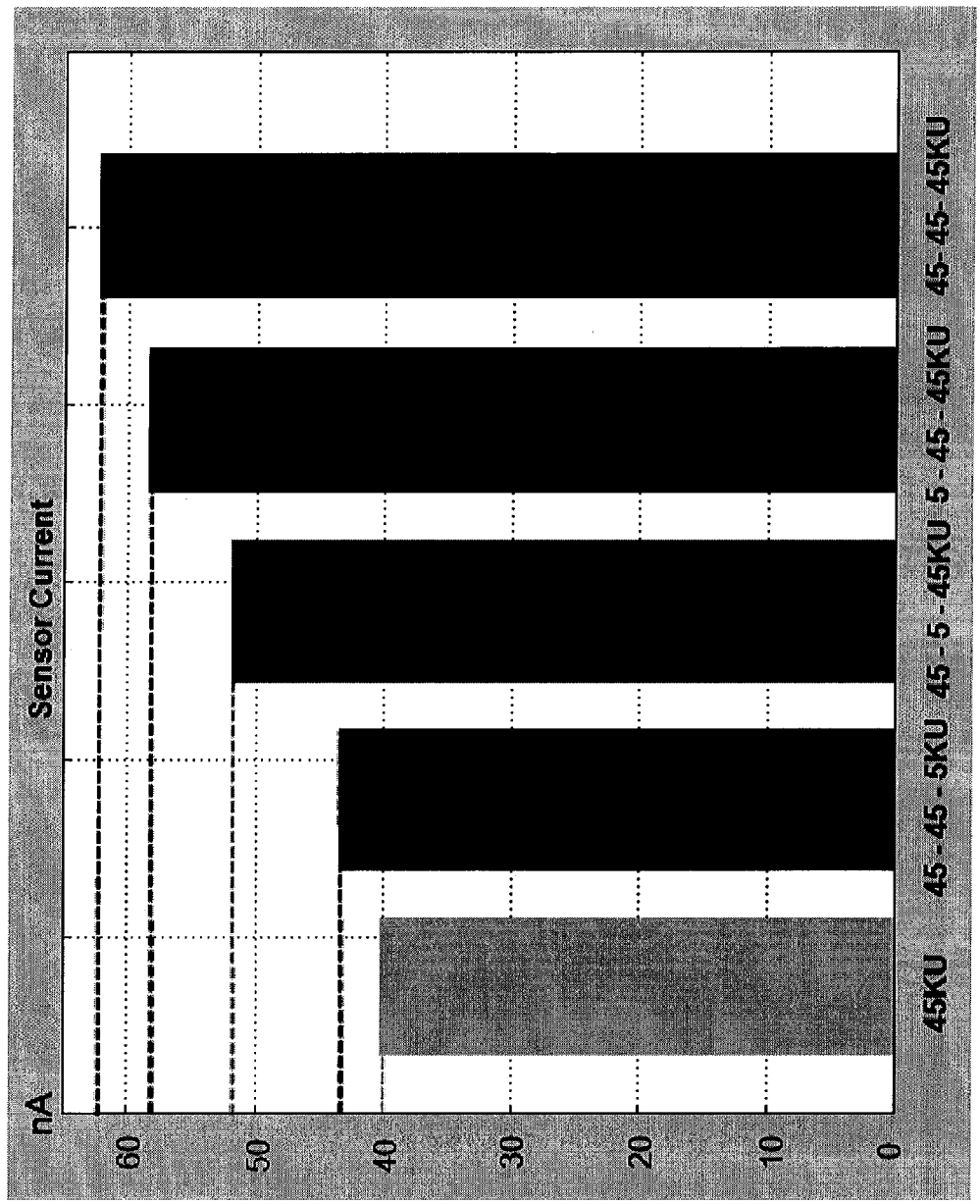

As shown for example by the data in FIGS. 8B-8D, glucose sensors having a plurality of layers of glucose oxidase at differing concentrations can form compositions which can generate an $H_2O_2$ signal at a sensor electrode that is optimized to quantify associated glucose levels while at the same time can reduce potential damage to the oxidoreductase. For example, as shown in FIGS. 8B-8D, the 5 KU-45 KU-45 KU layer and the 45 KU-45 KU-45 KU layer exhibit functionally comparable sensor characteristics even though the 5 KU-45 KU-45 KU layer comprises significantly less GOx than the 45 KU-45 KU-45 KU layer. Because the 5 KU-45 KU-45 KU layer comprises significantly less GOx however, it generates less H2O2 than does the 45 KU-45 KU-45 KU layer (H2O2 that can damage the GOx). In this way, H2O2 mediated damage to the GOx enzyme can be reduced while maintaining sensor signaling functions. Without being bound by a specific phenomena or scientific principle, it is believed that this observed effect may result from the layers of glucose oxidase at differing concentrations (e.g. 5 KU-45 KU-45 KU) influencing the flux of H2O2 molecules that are migrating to the electrode (e.g. the flux angle) in a manner that optimizes the sensor signal (even with significantly less GOx than a 45 KU-45 KU-45 KU layer).

Embodiments of the sensor disclosed herein include a subcutaneous amperometric glucose sensor which comprises membrane layers including glucose oxidase (GOx) layer(s), a human serum albumin (HSA) layer, an adhesion promoter (AP) layer, and a glucose limiting membrane (GLM) layer, all of which are typically applied on top of a sensor circuit (e.g. a three electrode flex circuit). In this sensor embodiment, the GLM acts as an analyte modulating layer to ensure that the GOx-glucose reaction is limited by the concentration of glucose and not $O_2$ as the GOx reaction produces hydrogen peroxide, which is then oxidized by the anodic working electrode to generate a measurable signal. These layers exhibit different permeability to substrates and product, and the relative concentrations of glucose and enzyme within the GOx layer(s) can affect the efficiency of the enzyme reaction. A mathematical model of single/multiple enzyme layer glucose sensor was developed with COMSOL Multiphysics® 3.5a and its chemical engineering module (and the data generated by this model is shown in FIGS. 8C-8D). In these modeling studies, the diffusion of substrate (glucose) and product (hydrogen peroxide) in the sensor membrane(s) is modeled by Fick's laws of diffusion (equation 1); the enzyme reaction is modeled by Michaelis-Menten enzyme kinetics (equation 2); and the sensor's current value is calculated by equation 3.

$$\frac{\partial C(x,t)}{\partial t} = D \frac{\partial^2 C(x,t)}{\partial x^2} \quad \text{Equation 1}$$

In equation 1, D is the diffusion coefficient, C is the concentration, x is thickness, and t is time.

$$\frac{K_{cat} \cdot C_{GOx} \cdot C_{Glucose}}{K_m + C_{Glucose}} \quad \text{Equation 2}$$

In equation 2, Km is the Michaelis-Menten constant and Kcat is the catalytic constant.

$$i(t) = n_e F A D_{H2O2} \frac{\partial C_{H2O2}}{\partial x} \quad \text{Equation 3}$$

In equation 3, $n_e$ is a number of electrons involved in a charge transfer at the electrode surface during the enzymatic reaction; F is the Faraday constant; and A is sensor surface area. Illustrative diffusion parameters that can be used in such models include the following: a thickness of GOx=1 E-6 m for single layer and 3 E-6 m total for triple layer (1 E-6 m for each individual layer); a diffusion coefficient of glucose in GOx=1.9 E-13 $m^2/s$; and a diffusion coefficient of hydrogen peroxide from GOx=4.6 E-13 $m^2/s$; where the Km=22 mM; the Kcat=6/s; ne=2; F=96,485 C/mol; and A=7.824 E-7 $m^2$. The parameters were set in sub-domain settings in membrane layer. For boundary settings in a typical model, a concentration of hydrogen peroxide is equal to zero at the sensor/bulk solution interface, a concentration of glucose is equal to 0.1375 mol/m3 (which equals to 2.5 mg/dl) at the sensor/bulk solution interface, a flux of glucose is equal to zero at the GOx/electrode interface, and a concentration of hydrogen peroxide is equal to zero at the GOx/electrode interface. By using this sensor model, one can demonstrate the beneficial multiple enzyme layer effects (e.g. directing the GOx reaction product flux angle and decreasing the product concentration proximal to GOx).

FIG. 8A, shows the results of a sensor in vitro test using a bicarbonate testing system at a temperature range of 36~37 C. The data in FIG. 8A shows the sensor response with different glucose concentrations and the associated Isig (40 na for 2.5 mg/dl glucose, 80 for 5.0 mg/dl, and 120 for 7.5 mg/dl), data providing evidence that the sensor linearity is appropriate. FIG. 8C provides modeling data showing a comparison all the H2O2 flux(angles) of various layered GOx compositions.

FIG. 8D shows sensor current values for of various layered GOx compositions having different enzyme concentration, based on the sensor current value calculation. In FIGS. 8B, 8C and 8D, x=0 indicates that, in the bulk/sensor interface, the right side of the figure corresponds to the electrode surface. As shown for example by the data presented in FIGS. 8B, 8C and 8D, in certain embodiments of the invention, the layer having the highest concentration of enzyme is disposed closest to electrode surface. Those of skill in the art understand that other models and or model parameters known in the art can be readily adapted for evaluating sensor layers having various GOx concentrations.

Embodiments of the invention having multiple layers of oxidoreductases such as glucose oxidase include an amperometric analyte sensor apparatus comprising a base layer, a conductive layer disposed on the base layer and comprising a working electrode (optionally comprising a sputtered platinum composition or one or more other elements discussed in the preceding paragraphs). In illustrative embodiments, a first analyte sensing layer comprising a first concentration of glucose oxidase is disposed on/over the conductive layer (e.g. in direct or indirect contact with the electroactive surface of an electrode). A second analyte sensing layer comprising a second concentration of glucose oxidase is disposed over this first analyte sensing layer and a third analyte sensing layer comprising a third concentration of glucose oxidase is disposed over the second analyte sensing layer. Typically, an analyte modulating layer is then disposed over these first, second and third analyte sensing layers. Permutations of this arrangement include sensors having two analyte sensing layers as well as sensors having four, five, six or more analyte sensing layers.

In embodiments of the invention, the first concentration of glucose oxidase is typically greater than the second concentration of glucose oxidase (e.g. at least 5, 10, 20 or 30 KU greater than the adjacent layer). Similarly, in embodiments of the invention, the second concentration of glucose oxidase is typically greater than the third concentration of glucose oxidase (e.g. at least 5-20 KU greater than the adjacent layer). In one illustrative embodiment of this, the first concentration of glucose oxidase is between 35 KU/mL and 55 KU/mL; the second concentration of glucose oxidase is between 35 KU/mL and 55 KU/mL; and/or the third concentration of glucose oxidase is between 5 KU/mL and 25 KU/mL. Optionally in these layers, the glucose oxidase is entrapped within a matrix of UV crosslinked poly(vinyl alcohol)-styrylpyridinium (PVA-SbQ) polymers. The thickness of these layers can be varied. Optionally the thickness of the first analyte sensing layer is between 0.5 and 1.5 microns, the thickness of the second analyte sensing layer is between 0.5 and 1.5 microns; and/or the thickness of the third analyte sensing layer is between 0.5 and 1.5 microns. Certain embodiments of the invention can include modifying a surface of the analyte sensing layer using a plasma deposition process (e.g. a He or Ar plasma deposition process) so that chemical moieties on the surface of analyte sensing layer are crosslinked.

These analyte sensors can further comprising one or more additional elements such as an electrolyte retaining layer, a protein layer, an interference rejection membrane, an adhesion promoting layer; and/or a cover layer disposed over the analyte sensor apparatus, wherein the cover layer comprises an aperture positioned on the cover layer so as to facilitate an analyte present in the mammal contacting and diffusing through an analyte modulating layer; and contacting the analyte sensing layer. In embodiments, the working electrode comprises a sputtered platinum composition and the sensor apparatus further comprises an electrolyte retaining layer in operable contact with the conductive layer, wherein the electrolyte retaining layer is formed from a composition selected to absorb 10% to 50% water by weight. Optionally, the analyte modulating layer comprises a blended mixture of a linear polyurethane/polyurea polymer and a branched acrylate polymer blended together at a ratio of between 1:1 and 1:20 by weight %. In certain embodiments of the invention, the analyte modulating layer exhibits a permeability to glucose that changes less than 2% per degree centigrade over a temperature range of 22 to 40 degrees centigrade.

Another embodiment of the invention is a method of modulating a flux of hydrogen peroxide molecules within a layered glucose sensor apparatus, the method comprising organizing layers in the apparatus to comprise a base layer, a conductive layer disposed on the base layer and comprising a working electrode, a first analyte sensing layer disposed on the conductive layer and comprising a first concentration of glucose oxidase, a second analyte sensing layer disposed over the first analyte sensing layer and comprising a second concentration of glucose oxidase, a third analyte sensing layer disposed over the second analyte sensing layer and comprising a third concentration of glucose oxidase, and an analyte modulating layer disposed over the first, second and third analyte sensing layers. In such embodiments of the invention, the first, second and third concentrations of glucose oxidase within the first, second and third analyte sensing layers function to alter an angle of the flux of hydrogen peroxide molecules in the first second and third layers that is generated by glucose oxidase in the presence of glucose (e.g. as compared to a single layer or concentration of glucose oxidase) so that the flux of hydrogen peroxide molecules within the layered glucose sensor apparatus is modulated. Without being bound by a specific scientific theory or principle, in such embodiments, it is believed that the different levels of glucose oxidase in the first, second and third analyte sensing layers alters an angle of the flux of hydrogen peroxide molecules generated by glucose oxidase in the presence of glucose so that the flux of hydrogen peroxide molecules within the layered glucose sensor is optimally directed to an electroactive surface on the working electrode (e.g. as compared to a single layer or concentration of glucose oxidase, see, e.g. FIG. 8C).

Yet another embodiment of the invention is a composition of matter comprising a metallic electrode, a first analyte sensing layer disposed over the metallic electrode and comprising a first concentration of glucose oxidase, a second analyte sensing layer disposed over the first analyte sensing layer and comprising a second concentration of glucose oxidase, a third analyte sensing layer disposed over the second analyte sensing layer and comprising a third concentration of glucose oxidase and an analyte modulating layer disposed over the first, second and third analyte sensing layers.

Embodiments of the invention include understandably methods of sensing an analyte within the body of a mammal, the method comprising implanting an analyte sensor embodiment disclosed herein in to the mammal and then sensing one or more electrical fluctuations such as alteration in current at the working electrode and correlating the alteration in current with the presence of the analyte, so that the analyte is sensed. In one such method, the analyte sensor apparatus senses glucose in the mammal. In an alternative method, the analyte sensor apparatus senses lactate, potassium, calcium, oxygen, pH, and/or any physiologically relevant analyte in the mammal.

A. Typical Sensor Architectures Found in Embodiments of the Invention

FIG. 2A illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2A includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensore 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2A, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. In the sensor configuration shown in FIG. 2B, an interference rejection membrane 120 is disposed on one or more of the exposed electrodes of the conductive layer 104, with the analyte sensing layer 110 then being disposed on this interference rejection membrane 120. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (µm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a sputtered platinum electrode), as well as spin coating processes, dip and dry processes, low shear spraying processes, ink-jet printing processes, silk screen processes and the like.

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte access with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, NAFION, polyester sulfonic acids (e.g. Kodak AQ), hydrogels or any other suitable hydrophilic membranes known to those skilled in the art.

In some embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

Embodiments of typical elements used to make the sensors disclosed herein are discussed below.

B. Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 2A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2A, the base constituent 102 comprises a ceramic. Alternatively, the base constituent comprises a polymeric material such as a polyimidide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed (see, e.g. element 104 in FIG. 2A). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include sputtered platinum electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively an electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/ or counter/reference electrodes. One embodiment of the sensor of the present invention has two, three or four or more working electrodes. These working electrodes in the sensor may be integrally connected or they may be kept separate.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as the hydrophilic crosslinked pHEMA and polylysine polymers disclosed herein (see, e.g. the Examples below) as well as cellulose acetate (including cellulose acetate incorporating agents such as poly(ethylene glycol)), polyethersulfones, polytetra-fluoroethylenes, the perfluorinated ionomer NAFION, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those disclosed for example in U.S. Pat. No. 5,755,939 and U.S. patent application Ser. No. 12/572,087, the contents of which are incorporated by reference. FIG. 2B shows an embodiment of the invention comprising a interference rejection membrane.

Analyte Sensing Constituent

The electrochemical sensors of the invention include an analyte sensing constituent disposed on the electrodes of the sensor (see, e.g. element 110 in FIG. 2A). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode in one or more layers to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is detected at the working electrode in the conductive constituent.

As noted above, layers comprising the enzyme and the second protein (e.g. an albumin) can be treated to form a crosslinked matrix (e.g. by UV crosslinking or by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture.

Protein Constituent

The electrochemical sensors of the invention optionally include a protein constituent disposed between the analyte sensing constituent and the analyte modulating constituent (see, e.g. element 116 in FIG. 2A). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2A). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as 3-aminopropyltriethoxysilane.

The use of silane coupling reagents, especially those of the formula R'Si(OR)$_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as 3-aminopropyltriethoxysilane and glutaraldehyde were used in a step-wise process to attach and to co-crosslink bovine serum albumin (BSA) and glucose oxidase (GOx) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2A). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane (e.g. a glucose limiting membrane) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868, 5,391,250 and U.S. patent application Ser. No. 12/643,790, the disclosures of each being incorporated herein by reference.

Cover Constituent

The electrochemical sensors of the invention include one or more cover constituents which are typically electrically insulating protective constituents (see, e.g. element 106 in FIG. 2A). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photo-imageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors disclosed herein can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver periodically (e.g. every 5 minutes) to provide providing real-time sensor glucose (SG) values. Values/graphs are displayed on a monitor of the pump receiver so that a user can self monitor blood glucose and deliver insulin using their own insulin pump. Typically an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values includes a plurality of measurements of blood glucose.

D. Embodiments of the Invention and Associated Characteristics

Embodiments of the invention disclosed herein focus on implantable analyte sensors and sensor systems that are designed to include sputtered platinum electrodes, electrolyte retaining compositions (e.g. an interference rejection membrane comprising crosslinked polymers) and/or configurations of elements that facilitate sensor initialization and/or start-up in vivo (e.g. the run-in time that it takes for a sensor to settle into its aqueous environment and start transmitting meaningful information after being implanted in vivo). In particular, it is known in the art that the amount time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin). In addition, a relatively long sensor initialization and/or start-up period in hospital settings can require repeated monitoring by hospital staff, a factor which contributes to the costs of patient care. For these reasons, sensors having reduced initialization and/or start-up times in vivo in hospital settings and sensors and sensor systems that are designed to include elements and/or configurations of elements that diminish long sensor initialization and/or start-up times are highly desirable. With glucose sensors for example, a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. The use of glucose sensors, insulin infusion pumps and the like in the management of diabetes has increased in recent years due for example to studies showing that the morbidity and mortality issues associated with this chronic disease decrease dramatically when a patient administers insulin in a manner that closely matches the rise and fall of physiological insulin concentrations in healthy individuals. Consequently, patients who suffer from chronic diseases such as diabetes are instructed by medical personnel to play an active role in the management of their disease, in particular, the close monitoring and modulation of blood glucose levels. In this context, because many diabetics do not have medical training, they may forgo optimal monitoring and modulation of blood glucose levels due to complexities associated with such management, for example, a two hour start-up period which can be an inconvenience in view of a patient's active daily routine. For these reasons, sensors and sensor systems that are designed to include elements and/or configurations of elements can reduce sensor initialization and/or start-up times (e.g. the hydrophilic interference rejection membranes disclosed herein) are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As disclosed herein, those of skill in the art understand that a conductive layer disposed on the base layer and comprising a sputtered platinum working electrode, a counter electrode and a reference electrode includes embodiments wherein the conductive layer is disposed on at least a portion the base layer and does not necessarily completely cover the base layer. Those of skill in the art will understand that this refers to other layers within the sensor, with for example, an analyte sensing layer disposed on the conductive layer encompassing sensor embodiments where the analyte sensing layer disposed on at least a portion of the conductive layer; and an analyte modulating layer disposed on the analyte sensing encompassing an analyte modulating layer disposed on at least a portion of the analyte sensing etc. etc. Optionally, the electrodes can be disposed on a single surface or side of the sensor structure. Alternatively, the electrodes can be disposed on a multiple surfaces or sides of the sensor structure (and can for example be connected by vias through the sensor material (s) to the surfaces on which the electrodes are disposed). In certain embodiments of the invention, the reactive surfaces of the electrodes are of different relative areas/sizes, for example a 1X reference electrode, a 1.75X working electrode and a 3.6X counter electrode.

In certain embodiments of the invention, an element of the apparatus such as an electrode or an aperture is designed to have a specific configuration and/or is made from a specific material and/or is positioned relative to the other elements so as to facilitate a function of the sensor. For example, without being bound by a specific theory or mechanism of action, it appears that sensor embodiments (e.g. simple three electrode embodiments) may be more susceptible to local environment changes around a single electrode. For example, a gas bubble on top of or close to a reference or another electrode, and/or a stagnating or semi-stagnating pool of fluid on top of or close to a reference or another electrode may consequently compromises sensor performance. In this context, a distributed electrode configuration appears be advantageous because the distribution of the electrode area allows the sensor to compensate for signal lost to a small local area (e.g. as can occur due to lack of hydration, fluid stagnation, a patient's immune response, or the like).

Some analyte sensor apparatus embodiments comprises a plurality of working electrodes, counter electrodes and reference electrodes. Optionally, the plurality of working, counter and reference electrodes are grouped together as a unit and positionally distributed on the conductive layer in a repeating pattern of units. Alternatively, the plurality of working, counter and reference electrodes are grouped together and positionally distributed on the conductive layer in a non-repeating pattern of units. In certain embodiments of the invention, the elongated base layer is made from a material that allows the sensor to twist and bend when implanted in vivo; and the electrodes are grouped in a configuration that facilitates an in vivo fluid accessing at least one of working electrode as the sensor apparatus twists and bends when implanted in vivo. In some embodiments, the electrodes are grouped in a configuration that allows the sensor to continue to maintain an optimal function if a portion of the sensor having one or more electrodes is dislodged from an in vivo environment and exposed to an ex vivo environment.

In typical embodiments of the invention, the sensor is operatively coupled to further elements (e.g. electronic components) such as elements designed to transmit and/or receive a signal, monitors, pumps, processors and the like (see, e.g. U.S. Pat. Nos. 6,558,351, 7,344,500 and 7,278,983, the contents of which are incorporated herein by reference). For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode.

In some embodiments of sensors insertion set apparatuses, a first and a second (and/or third etc.) electrochemical sensor comprises one working, counter and reference electrode. Alternatively, the plurality of electrochemical sensors comprise a plurality of working, counter and reference electrodes, for example those having a distributed configuration as disclosed in U.S. patent application Ser. No. 11/633,254, the contents of which are incorporated by reference. In certain embodiments of the invention, at least two in the plurality of sensors are designed to measure a signal generated by the same physiological characteristic, for example blood glucose concentration. Embodiments of the invention can include for example a plurality of electrochemical sensors having a working electrode coated with an oxidoreductase such as glucose oxidase and are used in methods designed to sample and compare glucose concentrations observed at the plurality of in vivo insertion sites. Alternatively, at least two in the plurality of sensors in the sensor apparatus are designed to measure signals generated by the different characteristics, for example a first characteristic comprising a background or interfering signal that is unrelated to blood glucose (e.g. "interferent noise") and a second characteristic comprising blood glucose concentrations. In an illustrative embodiment of this invention, a first sensor is designed to measure glucose oxidase and comprises one or more working electrodes coated with glucose oxidase while a second comparative sensor is designed to measure a background or interfering signal that is unrelated to blood glucose has no working electrode (or electrodes) coated with glucose oxidase.

In certain embodiments of the invention, sensor systems that utilize voltage pulsing and/or switching as disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that utilize voltage pulsing and/or switching can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, etc.).

In some embodiments of the invention, a processor is capable of comparing a first signal received from a working electrode in response to a first working potential with a second signal received from a working electrode in response to a second working potential, wherein the comparison of the first and second signals at the first and second working potentials can be used to identify a signal generated by an interfering compound. In one such embodiment of the invention, one working electrode is coated with glucose oxidase and another is not, and the interfering compound is acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides or uric acid. Optionally, a pulsed and/or varied (e.g. switched) voltage is used to obtain a signal from a working electrode. Typically, at least one voltage is 280, 535 or 635 millivolts. Related embodiments of the invention include methods for identifying and/or characterizing one or more signals generated by an interfering compound in various sensor embodiments of the invention (e.g. by comparing the signal from an electrode coated with an analyte sensing compound with a comparative electrode not coated with an analyte sensing compound). Optionally, such methods use a pulsed and/or varied working potential to observe a signal at an electrode.

Sensors of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a sputtered platinum working electrode, a reference electrode and a counter electrode); forming a electrolyte maintaining layer and/or an interference rejection membrane on the conductive layer, forming an analyte sensing layer on the interference rejection membrane, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration.

As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

B. Typical Protocols and Materials Useful in the Manufacture of Analyte Sensors

The disclosure provided herein includes sensor materials and sensor designs that can be generated using combinations of various well known techniques. For example, the disclosure describes electrode compositions formed form sputtered platinum and sensors produced using such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface. Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements include one or more sputtered platinum electrodes that are formed by one of the variety of methods known in the art. Further layers such as electrolyte maintaining layers and/or IRMs and analyte sensing enzyme layers etc. can then be disposed on the sensing layer by electrochemical deposition or a method other than electrochemical deposition such a spin coating, followed by vapor crosslinking, for example with a dialdehyde (glutaraldehyde) or a carbodi-imide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including sputtering methodologies. Such a metal deposition processes should yield a structure with good metal to metal adhesion and minimal surface contamination, however, to provide a catalytic metal electrode surface with reasonable number of active sites.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the sensor are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

In an illustrative sensor embodiment for use as a glucose sensor, an enzyme (typically glucose oxidase) is coated with the enzyme so as to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor. Methods for producing the enzyme coatings include spin coating processes, dip and dry processes, low shear spraying processes, ink-jet printing processes, silk screen processes and the like. Optionally, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as 3-aminopropyltriethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

One illustrative embodiment of the invention is a method of making a sensor electrode by providing an sputtered platinum electroactive surface which functions as an electrode, forming an electrolyte maintaining layer and/or an interference rejection membrane on the electroactive surface, spin coating an enzyme layer on this layer and then forming an analyte contacting layer (e.g. an analyte modulating layer such as a glucose limiting membrane) on the electrode, wherein the analyte contacting layer regulates the amount of analyte that can contact the enzyme layer. In some methods, the enzyme layer is vapor crosslinked on the sensor layer. In a typical embodiment of the invention, a sensor is formed to include at least one working electrode and at least one counter electrode. In certain embodiments, the IRM is formed on at least a portion of the working electrode and at least a portion of the counter electrode. Typically, the enzyme layer comprises one or more enzymes such as glucose oxidase, glucose dehydrogenase, lactate oxidase, hexokinase or lactate dehydrogenase and/or like enzymes. In a specific method, the enzyme layer comprises glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, a layer such as the IRM and/or the adhesion promoter layer is subjected to a curing process prior to the formation of the analyte contacting layer.

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. The functional coating layer(s) can be applied either before or after other sensor components are removed from the supporting substrate (e.g., by cutting).

III. Kits and Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container comprises an electrode matrix composition that includes a layer of an enzyme such as glucose oxidase. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

Various publication citations are referenced throughout the specification. The disclosures of all citations in the specification are expressly incorporated herein by reference. These disclosures include, for example, Slavcheva et al., Applied Surface Science 255 (2009) 6479-6486; Maley et al., Bioelectrochemistry 63 (2004) 359-364; van O S et al., Analytica Chimica Acta 335 (1996) 209-216; Pfeiffer et al., *Biosensors & Bioelectronics* Vol. 12. No. 6, pp. 539-550, 1997; Osaka, T., "Electrochemical formation and microstructure in the films for high functional devices," Electrochimica Acta, vol. 42, nos. 20-22, pp. 3015-3022, 1997; de Haro, C. et al., "Electrochemical platinum coatings for improving performance of implantable microelectrode arrays," Biomaterials 23 (2002) 4515-4521; Jacobs, P. et al., "Nanometer size platinum particle arrays: catalytic and surface chemical properties," Surface Science 372 (1997) L249-L253; Yang, M. et al., "Platinum nanowire nanoelectrode array for the fabrication of biosensors," Biomaterials 27 (2006) 5944-5950; Pak, S. et al., "An ultrathin platinum film sensor to measure biomolecular binding," Biosensors & Bioelectronics 16 (2001) 371-379; Laschi, S. et al., "Planar electrochemical sensors for biomedical applications," Medical Engineering & Physics 28 (2006) 934-943; Patel, N. et al., "Fabrication and characterization of disposable type lactate oxidase sensors for dairy products and clinical analysis," Sensors and Actuators B 67 (2000) 134-141; Sberveglieri, G., "Recent developments in semiconducting thin-film gas sensors," Sensors and Actuators B 23 (1995) 103-109; Lee, C. et al., "Comparison of amperometric biosensors fabricated by palladium sputtering, palladium electrodeposition and Nafion/carbon nanotube casting on screen-printed carbon electrodes," Biosensors and Bioelectronics 22 (2007) 877-884; Chou, N. et al., "Differential type solid-state urea biosensors based on ion-selective electrodes," Sensors and Actuators B 130 (2008) 359-366; Martinez, C. et al., "Electrochemical and geometrical characterization of iridium oxide electrodes in stainless steel substrate," Sensors and Actuators B 133 (2008) 682-686; Wilson, G. et al., "Biosensors for real-time in vivo measurements," Biosensors and Bioelectronics 20 (2005) 2388-2403; Ges, I. et al., "Thin-film IrO$_x$ pH microelectrode for microfluidic-based microsystems," Biosensors and Bioelectronics 21 (2005) 248-256; Huang, I. et al., "Fabrication and characterization of a new planar solid-state reference electrode for ISFET sensors," Thin Solid Films 406 (2002) 255-261; Madaras, M. et al., "Microfabricated amperometric creatine and creatinine biosensors," Analytica Chimica Acta 319 (1996) 335-345; and Pfeiffer, D. et al., "Amperometric lactate oxidase catheter for real-time lactate monitoring based on thin film technology," Biosensors & Bioelectronics, vol. 12, no. 6, pp. 539-550, 1997.

EXAMPLES

Example 1

Low Isig Sputtered Platinum Sensors

This Example illustrates the development of low Isig ~5 nA/100 mg/dL sensors using sputtered Pt as working electrode for implantable applications. In particular, this Example describes the development of low Isig glucose sensors with various geometries or design layouts of sputtered Pt working electrode. As part of this, the disclosure below identifies illustrative ways to create, modify and/or optimize membrane chemistry useful in functional sensors adapted for in vitro and in vivo applications. General aspects of this technology are described in U.S. Pat. Nos. 5,837,446, 6,136,463 and 7,488,548, the contents of which are incorporated by reference.

Aspects of this invention pertain to amperometric glucose sensors and use terms such as "Isig", which is an acronym for Interstitial SIGnal. Isig value is proportional to the blood glucose value. If you take the isig value and multiply it by a calibration factor, this will give you the blood glucose reading in mg/dL. Isig values are actually nA (nano amps)—so it is an electric measurement value, the Isig value will drop and rise as glucose levels drop and rise. Low Isig typically means less intense electrochemical reaction inside of the body which would maintain a stable chemical environment longer.

In electrode characterizations of amperometric glucose sensors, experimental result with working electrodes formed from a sputtered Pt composition show a close to zero background current with about half of the Isig responses with the same geometric working electrode area of Pt black sensors. This characteristic provides evidence that sputtered Pt compositions may be a better material for forming working electrodes within glucose sensors due to a higher accuracy at lower glucose concentration ranges, a feature that will allow for the safer monitoring of hypoglycemic patients.

Isig levels observed in typical glucose sensors can range from pico-amps to ten's nano-amps depending upon the applications in which the sensor is used. Low Isig doesn't mean low accuracy. Contrarily, it can provide sensors with a longer life expectancy as long as background current and system noise are sufficiently low. As part of this, we demonstrate how to fine and tune the membrane chemistry to get the best sensor performance in vitro and in vivo for sputtered Pt electrodes.

Basic Electrochemical Parameters

The determination of glucose is accomplished by the following set of reactions:

Glucose reaches the enzyme, where it is oxidized to gluconic acid by oxygen, leaving H2O2. One molecule of glucose gives one molecule of H2O2 at the expense of one molecule of oxygen:

$$C_6H_{12}O_6+H_2O+O_2 \rightarrow C_5H_{11}O_5COOH+H_2O_2 \qquad (1)$$

At the working electrode H2O2 is oxidized and the oxygen is regenerated:

$$H2O2 \rightarrow O2+2H++2e^- \qquad (2)$$

The enzymatically generated H2O2 reaches the working electrode the oxygen is fully recovered.

At the counter electrode a reduction process occurs such as the following 3 examples:

$$2H2O+2e- \rightarrow H2+2OH— \qquad (3)$$

$$H2O2+2e- \rightarrow 2OH— \qquad (4)$$

$$\tfrac{1}{2}O2+2H++2e- \rightarrow H2O \qquad (5)$$

Reaction (3) is believed to be occurring in such systems, as the sensor will always contain water. Any of the three reactions on the counter electrode will serve to neutralize the protons generated in reaction (2), so the total increase in acidity is caused by the gluconic acid only. The net reaction when the sensor is working is then production of gluconic acid and H2 (at the expense of glucose and H2O).

Working Electrode (WE) Potential Selection

In typical embodiments of the invention, the electrical potential for the working electrode has to be high enough to assure fast oxidation of H2O2, yet low enough to minimize background current from oxidation of water and solution components. In addition, the signal to noise ratio should be within a reasonable range. In such systems, the linearity can be improved by increasing the polarization potential if necessary. As described herein, general sensor performance improves significantly by controlling the membrane systems used with sputtered Pt electrodes.

Counter Electrode (CE) Area Determination

CE surface area is typically large enough to avoid any limiting currents from this part of the sensor. In this context, cyclic voltammetry experiments can be performed to ensure that the actual size of the CE is large enough.

Reference Electrode (RE) Area and Character Determination

Typically, the requirements for an Ag/AgCl layer on a RE are high capacity of AgCl, high conductivity, and high resistance to the alcohol. The high capacity is important because the polarization potential will change in case all the AgCl dissolves. The stability of the reference electrode can be examined by measuring the potential against an external reference electrode during the operational 7 day testing period.

Basic Membrane Chemistry

In typical embodiments of the invention, the sensor membrane structure comprises a IRM or/and electrolyte maintaining layer, an immobilized enzyme layer and glucose limiting membrane (to get an appropriate linearity, pO2 permeability and biocompatibility). An adhesion promoter (AP) can be included in some embodiments.

Electrolyte Retaining/Maintaining Layer/Membrane

In certain embodiments of the invention, a layer/membrane comprising a pool of electrolytes, for example with an appropriate Cl$^-$ ion concentration, pH buffer capacity and general ion strength can be used to maintain optimal electrochemistry and biochemistry parameters during the sensing process. This layer/membrane can be very significant in vivo due to the long sensing times for electrochemical and biochemical reactions, especially those with a with a relatively higher detecting Isig. Maintaining a comparable Isig level in vivo as in vitro and also a stable Isig during sensing process is important.

Typical requirements for this layer include certain amount of water adsorption, typically enough adsorption to maintain and optimize sensor electrochemistry for the in vivo life time of the sensor. Isig level and stability are illustrative parameters used to assess the layer's function. While this layer/membrane can be used to overcome difficulties with electrodes made from sputtered Pt compositions, the need for such as layer is not the same with Pt black electrode due to the porosity of the Pt black structure (which provides an environment for electrolytes). For electrodes made from sputtered Pt compositions, one material that can provide the necessary electrolyte environment is the analyte sensing (e.g. GOx) layer.

A variety of materials can be used to form an electrolyte maintaining layer used with electrodes made from sputtered Pt compositions. For example, the material can be formed from a hydrophilic polymer having 10 to 50% water adsorption by weight. The material can be formed from a cross linked polymer matrix with entrapped hydrophilic polymer component to provide appropriate water adsorption. Typical selections include hydrophilic polyurethane (PU), crosslinked BSA (bovine serum albumin) with entrapped hydrophilic polymers such as methylcellulose (MC) or polyvinylpyrolidione (PVP) etc., interference rejection membranes (IRMs) and analyte sensing layers can also provide water adsorption capabilities.

Crosslinked GOx Layers

Standard Glutaraldehyde Crosslinking

Immobilization of GOx by covalent attachment to water-insoluble carriers via glutaraldehyde is a simple and gentle coupling methods in enzyme technology. Glutaraldehyde was widely used as a mild cross-linking agent for the immobilization of enzymes because the reaction proceeds in aqueous buffer solution under conditions close to physiological pH, ionic strength, and temperature. The formation of a three-dimensional network as a result of intermolecular crosslinking and binding to an insoluble polyimide carrier constitutes a stable enzyme layer.

Enzyme Entrapment within PVA-SbQ Matrices

Enzymes such as GOx can also be immobilized within water-insoluble carriers via other processes known in the art, for example PVA-SbQ polymer matrix crosslinking. PVA-SbQ is polyvinyl alcohol functionalized with methyl pyridinium methyl sulfate. Enzymes can be immobilized within crosslinked polymer matrices of a PVA-SbQ photosensitive polymers having different molecular weights or grades (available from multiple vendors). The PVA-SbQ polymer crosslinking process can be done within seconds under UV exposure at ~365 nm wavelength. Following this process, the resulting polymer becomes less hydrophilic comparing with the pre-crosslinking condition.

Analyte Modulating Layer

Analyte modulating layers such as glucose limiting membranes can be used to provide a controlled glucose diffusion capability to the sensor system for extended response linearity. The glucose diffusion rate or Isig level can be adjusted by membrane hydrophilicity and membrane thickness. The glucose diffusion capacity of the membrane could also affect the system noise level and accuracy in vivo. The membrane water adsorption capacity can also be used control the Isig stability during the long term in vivo usage. In general the optimization of the membrane characters and thickness is important for sensor in vivo performance.

Illustrative Formulations and Experimental Methods

Electrolyte retaining layer: 4 g of 10% BSA in phosphate buffer of pH=7.4 with addition of 0.2 mL of 1% MC or 0.1 mL of 5% PVP.

Spin coating employed as the dispensing method:

POLYLYSINE IRM. Polylysine solution: 1% polylysine in DI H2O, molecular weight of polylysine ranged from 10 kd to 80 kd.

PolyHEMA IRM: 0.7% pHEMA in 95% C2H5OH and 5% H2O mixed with 0.41% BIS[3-(TRIETHOXYSILYL)PROPYLUREA.

Biodot spray method was applied for IRMs dispensing.

GOx are from standard 5% BSA or HSA formulation preparation.

The glucose limiting membrane (GLM) analyte modulating layer material comprises siliconized, PEG modified methacrylic copolymer.

Illustrative formulations analyte modulating layers useful with embodiments of the invention are disclosed for example in U.S. patent application Ser. No. 12/643,790, the contents of which are incorporated by reference.

Electrolyte Retaining Layers

BSA Based Layers

Figure 2C:
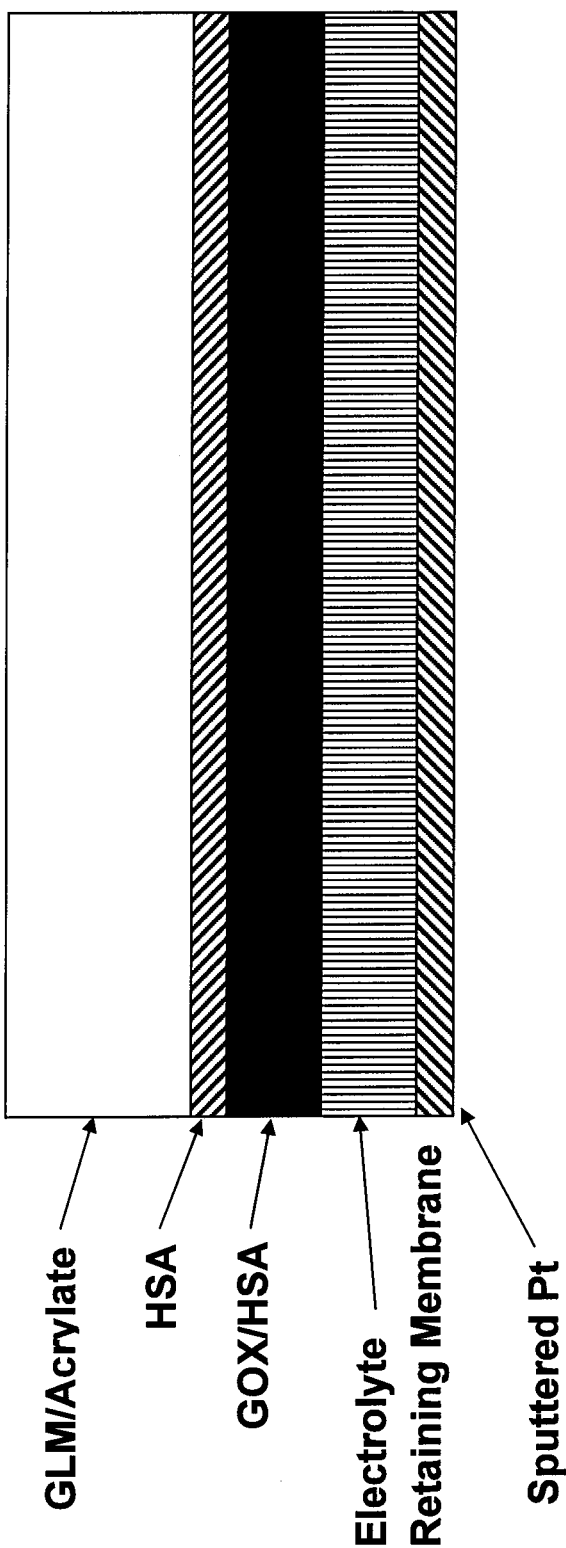
FIG. 2C provides a diagrammatic view of embodiments of an amperometric analyte sensor having an arrangement of layers comprising, from the bottom to the top of the figure, an electrode made from a sputtered platinum composition, a thin electrolyte retaining layer (e.g. one not more than 3, 4, 5, 6 or 7 μm thick), an analyte sensing layer comprising glucose oxidase (GOx) and human serum albumin (HSA), a protein layer comprising HSA, and an analyte modulating layer (in this embodiment a glucose limiting membrane comprising a blended mixture of linear polyurethane/polyurea polymers and branched acrylate polymers).
Figure 2D:
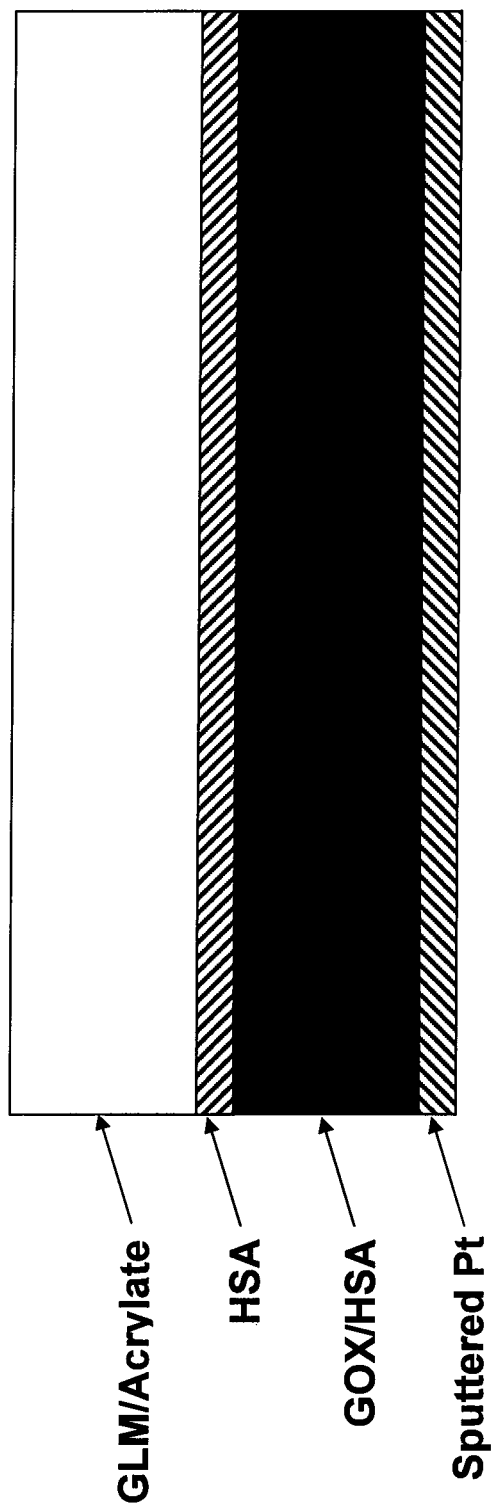
FIG. 2D provides a diagrammatic view of embodiments of an amperometric analyte sensor having an arrangement of layers comprising an electrode made from sputtered platinum, an analyte sensing layer comprising glucose oxidase (GOx) and human serum albumin (HSA), a protein layer comprising HSA, and an analyte modulating layer (in this embodiment a glucose limiting membrane comprising a blended mixture of linear polyurethane/polyurea polymers and branched acrylate polymers). Note that in FIG. 2D, the analyte sensing layer functions as the electrolyte retaining layer, and is typically somewhat thicker (e.g. 5, 6, 7, 8, 9 or 10 μm thick) than the thin electrolyte retaining layer shown in FIG. 2C.

Sensors having a BSA based electrolyte retaining layer were tested and shown to perform well and at equivalent Isig levels in vitro and in vivo. The Isig stability was particularly impressive with the addition of an extra BSA sub-layer disposed exactly in the sensor stack as shown in FIGS. 2C and 2D. Sensors with a single layer of GOx (20 ku/mL) with addition of BSA sub-layer also performed well. Consequently, the beneficial effects of the electrolyte retaining layer include both Isig level and stability. Absent this electrolyte retaining layer, the in vivo Isig level is much lower than the Isig level in vitro and is diminished soon after implant of the sensors.

PVA-SbQ Based Layers

Sensors were made with 500 rpm coated GOx layer, however the Isig level did maintained at the required level. MC added formulation performed better than PVP added one. Optimized Isig levels in dog are facilitated by the addition of the extra layer.

IRM Based Layers

Figure 3:
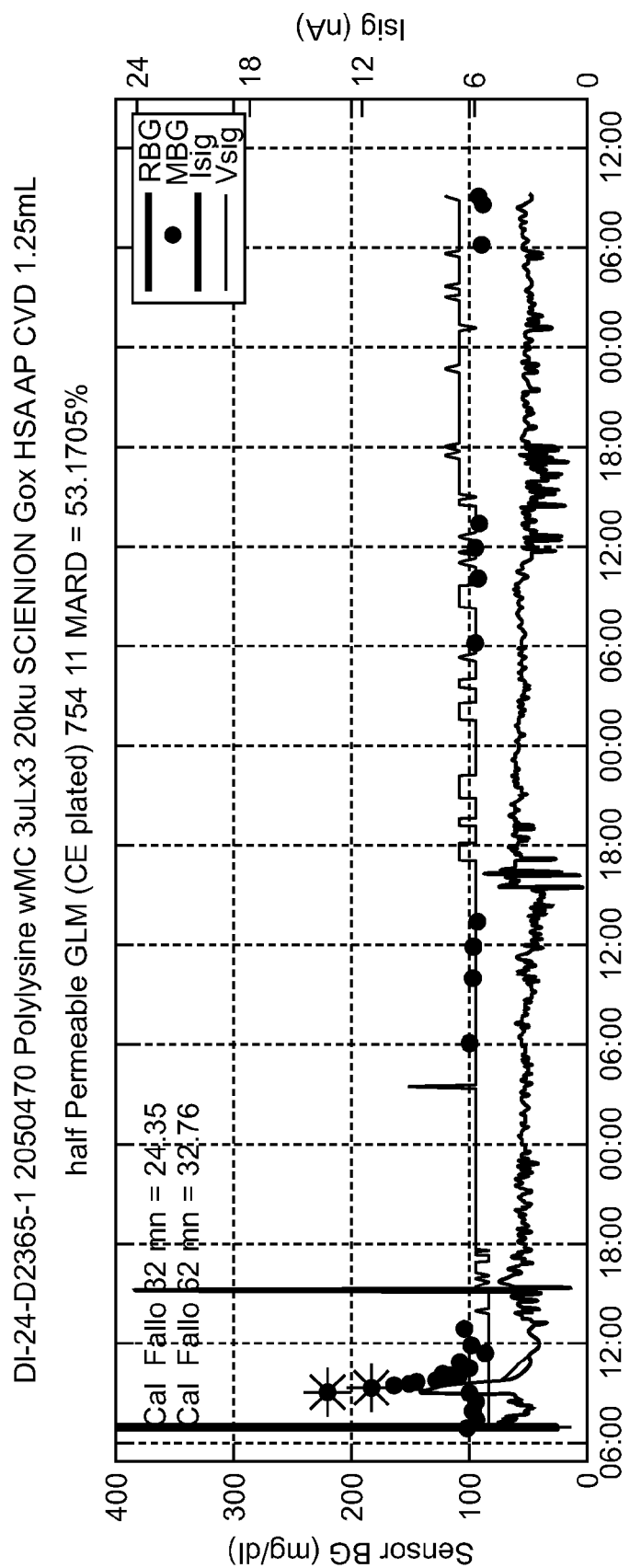
FIG. 3 provides a graph of glucose concentration data generated from an amperometric analyte sensor having an arrangement of layers comprising an electrode made from sputtered platinum, an interference rejection membrane formed from polylysine polymers, an analyte sensing layer comprising glucose oxidase (GOx) and human serum albumin (HSA), and an analyte modulating layer (in this embodiment a glucose limiting membrane comprising a blended mixture of linear polyurethane/polyurea polymers and branched acrylate polymers). The data in FIG. 3 shows sensors performed at significantly higher Isig level with a layer of polylysine polymers used as an interference rejection membrane (as compared to sensors lacking this IRM).
Figure 4:
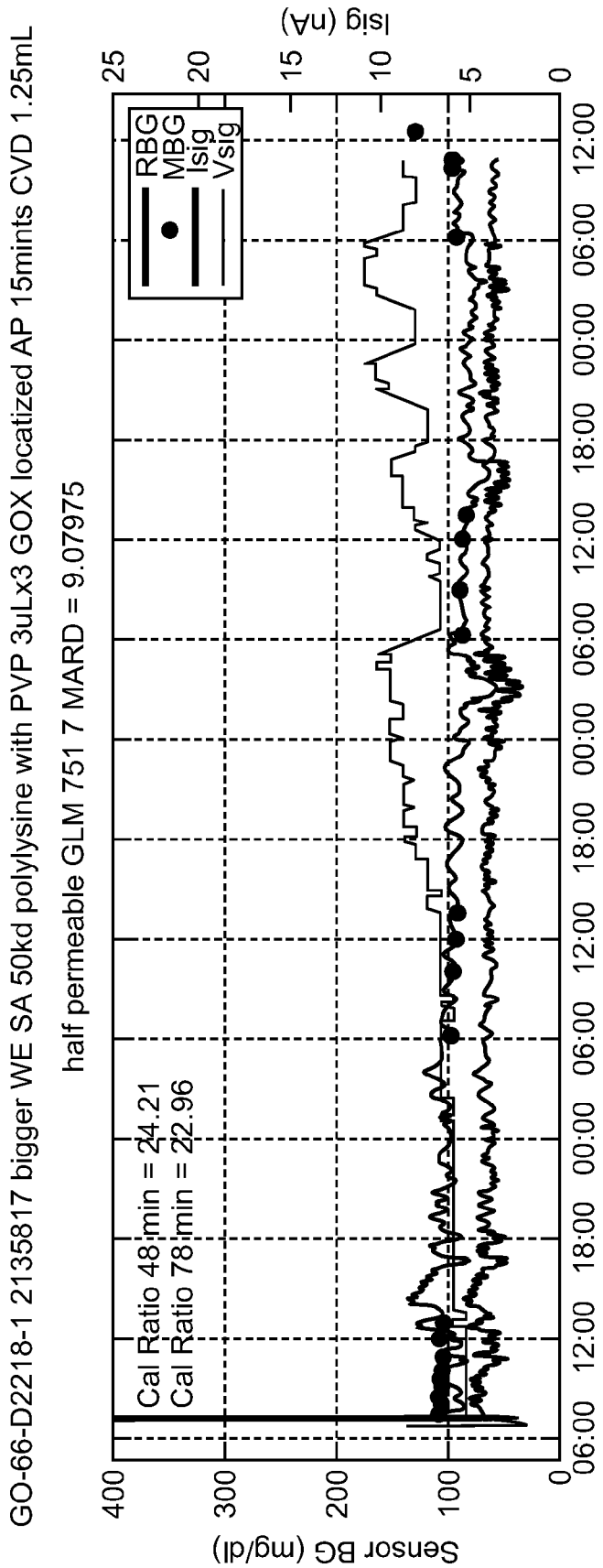
FIG. 4 provides a graph of glucose concentration data generated from a sensor comprising a working electrode formed from a sputtered platinum composition, an interference rejection membrane formed from polylysine polymers in combination with a poly-N-vinyl pyrrolidinone (PVP) polymer composition, an analyte sensing layer comprising glucose oxidase (GOx), and an analyte modulating layer (in this embodiment a glucose limiting membrane comprising a blended mixture of linear polyurethane/polyurea polymers and branched acrylate polymers). The data in FIG. 4 shows that the addition of PVP in polylysine layer expedites sensor initialization/start up. In addition, comparative studies further show that interference rejection membranes (IRMs) with 14 kD polylysine polymers exhibit a faster start-up profile than IRMs with 50 kD polylysine polymers.

The data in FIG. 3 shows sensors performed at significantly higher Isig level with a layer of polylysine. FIG. 4 showed the effect of addition of PVP in polylysine layer of expediting the initial start up. IRMs with 14 kd polylysine polymers exhibits a better start-up profile than IRMs with 50 kd polylysine polymers.

Crosslinked GOx Layers

Glutaraldehyde Crosslinked GOx

Standard thin layer of 0.5 um spin at 500 rpm usually produce perfect Isig in vitro, unfortunately the Isig level in vivo is much lower than in vitro. Some modulations of different GOx thickness yielded significant results.

Scienion Dispensed Thicker GOx Layer

Scienion is a pico-liter level liquid dispensing equipment. The layer thickness of GOx dispensed was at 2.5 um. Sensors made with thicker GOx layer produced a much higher responses than sensors with 0.5 um GOx layer.

Crosslinked PVA-SbQ Entrapped GOx Layer

PVA-SbQ entrapped GOx layer sensors responded well in non-diabetic dogs and in vitro test.

GLM Parameters

System Isig/noise level can determine the sensor Isig level required. GLM coating can directly affect the system noise level. The major affecting characters are membrane glucose permeability (or, membrane hydrophilicity/hydrophilicity) and membrane thickness.

Basic Membrane Character Considerations: Hydrophilicity Vs Hydrophobicity

Highly glucose permeable siliconized, PEG attached methacrylates as described in polymer group. The most significant advantage is its adhesive capability to the sub-layers with the potential of eliminating the need for APs. Apparently more hydrophilic membrane yielded higher Isig in vivo while they are using the same thickness. More water adsorption helps the sensor perform at a Isig level close to in vitro situation. GOx layer thickness is not the only factor determining the sensor in vivo Isig level. Isig could also be affected by the GLM.

GLM/acrylate Blends

Membrane permeability and corresponding thickness needed can be easily adjusted by various blending GLM/Acrylate ratio. Thin membrane with high permeability usually produced sensor with high noise in vivo. What is the acceptable mix ratio has to be determined by sensor in vivo performance.

In summary, a new sputtered Pt material has been fabricated and discovered to be a superior working electrode material for implantable glucose sensor applications due to its electrochemical characteristics such as low background current, reasonable high sensitivity, relatively low interference responses and system noise level.

A corresponding membrane chemistry and process were developed to yield a better in vitro and in vivo performance. Illustrative embodiments includes IRM and/or electrolyte retaining membrane, immobilized GOx membrane with 'HSA' membrane coverage and a GLM/Acrylic blend as a diffusion control membrane. AP layer was eliminated.

The sensor in vitro performed at a zero background current, sensitivity at 5-10 nA/100 mg/dL glucose level, with a linearity range up to at least 400 mg/dL. Sensor Isig level could be raised up to 20 nA/100 mg/dL by adjusting the electrode area or GLM permeability while low background current can still be maintained.

In vivo the sensor performed satisfactorily with a low noise, good sensor by sensor consistency, quick start and good accuracy. A significant advantage could be the accuracy at the lower glucose range for hypoglycemic patient for a better glucose level monitoring and control due to a low background current and low noise level. Another potential advantage could be more stable Isig and longer lifetime considering controlled low Isig level sensors.

Example 2

Further Characterization of Sputtered Pt Sensors

This Example provides data further characterizing the use of working electrodes formed from a sputtered Pt composition in as glucose sensors. In this context, cyclic voltammetry was developed to study the feasibility for our various applications.

The Example describes studies of sputtered Pt compositions on different substrates including Cr/Au and Ti/Au. In addition, the Example describes studies of sputtered Pt compositions on different geometries, different thickness and different mechanic layouts including electrodes of differing sizes (e.g. 2x3x). These studies examined the electrochemical characteristics of such sensors. Certain methods and materials that can be adapted to make embodiments of the invention are described for example in U.S. Pat. No. 5,837,446, and Japanese Patent No. JP63-101743 and JP62-261952, the contents of which are incorporated by reference.

To examine the use of an anode for electrochemical oxidation of $H_2O_2$ in a glucose sensor based on thin film techniques, several versions of sputtered Pt electrodes were evaluated by cyclic voltammetry in order to obtain comparable i/v characteristics. As a comparative reference, we compared pure Pt wire as well as standard electrodeposited Pt black used as working electrode compositions in sensors to demonstrate the advantages of different electrode material and processes.

Cyclic Voltammetry

Voltammetry is defined as a measuring technique where the current through the cell is recorded as a function of the applied potential. According to the applied potential waveform, different techniques can be distinguished. For example, in cyclic voltammetry a triangular potential waveform is applied to the electrochemical cell. Square wave voltammetry is a good example of a pulse method. Amperommetry is a special case of voltammetry, as in this technique the potential is kept constant.

In cyclic voltammetry (CV) the applied potential is changed linearly with time, starting from a potential where no electrode reaction occurs and moving to a potential where no electrode reaction occurs and moving to a potential where reduction or oxidation of the electroactive species involved occurs. After traversing the potential region where the electrode reaction take place, the scan direction is reversed and usually the electrode reactions of intermediates (i.e. products formed during the forward scan) are detected.

The important parameters of the cyclic voltammogram are: the cathodic and anodic peak potentials, the cathodic and anodic peak currents, the cathodic half-peak potential and half-wave potentials. The half-wave potential is usually situated within a few mV of the formal potential and provides valuable qualitative information of the electrochemical system involved. The potential peak separation also gives information on the reversibility of the electrode reaction. The difference between the anodic and cathodic peak potentials equals 59 mV per electron exchanged for a reversible system.

Basic Applications of Cyclic Voltammetry

Cyclic voltammetry is an electrochemical technique that is used to study the electrochemistry of solution species and in the study of electrochemical reactions with subsequent chemical reaction steps. The CV technique has also been widely applied in the study of modified electrodes qualitatively and quantitatively. It is not used for analytical applications.

For sensor applications, cyclic voltammetry can be used for the initial evaluation of new electrode materials or new technologies for electrode fabrication or process. With cyclic voltammetry experiments, the residual current of an electrode can be easily determined. In addition, leakage currents due to detective packaging can be detected. It is also a powerful tool for the investigation of adsorption effects.

Experimental Methods

Illustrative sensors tested from different lots of different fabrication processes are listed as the tables below:

TABLE 1

| Sensor specifications or fabrication parameters | | | | | | | |
|---|---|---|---|---|---|---|---|
| | 753 | 769 | 905-1 | 905-9 | 858 | Sputtered A Minimed | Pt black |
| Pattern | 2x3x | CS | 2x3x | 2x3x | 2x3x | 2x3x | 2x3x 2 |
| Size | std | Std CS | Std | Std | 1.75WE | 1.75WE | std |
| Thickness | std | Std CS | 2x std | Std | Std | Std | |
| Surface area (Roughness) | std | Std CS | std | 2Xstd | 1.75std | 1.75std | |
| Substrates | Cr/Au | Cr/Au | Ti/Au | Ti/Au | Cr/Au | Cr/Au | Cr/Au |

The H2O2 solution and acetaminophen used in the sensor studies, were analytical grade reagents purchased from Sigma-Aldrich. 0.1M H2O2 was used as stock solution. Initial background current scan was done in 50 mL physiological PBS buffer solution, with 0.5 mL, 0.5 mL, and 1 mL of stock H2O2 used to make 1 mM, 2 mM and 4 mM H2O2 solutions. Acetaminophen stock was used at 4 mM. Real test of 0.06 mM was made by adding 3 mL of stock solution to 50 mL of buffer solution to produce a reasonably high level of interference Isigs from all of the electrodes. The H2O2 solution needs to be made fresh daily. The surface area of Pt wire exposed to the solution is 2.46 mm$^2$ which is 6.37 times of standard 2x3x size of sputtered Pt electrode (0.387 mm$^2$).

During background current and H2O2 response scan processes, electrodes made from conventional original fabrications processes were used (e.g. platinum black for a working electrode). Later on it did show some current limitation due to the non-plated CE during the higher H2O2 concentration scan. In this case external Pt wire was used as CE instead. During acetaminophen scans external CE and reference electrodes were used to fairly evaluate the interference potential. The sweep rate was 10 mv/s in all cases. Prior to the sweeps the electrode was cycled three times in buffer solution before the actual background current scans were recorded.

Results And Discussions

Background Current

Figure 5:
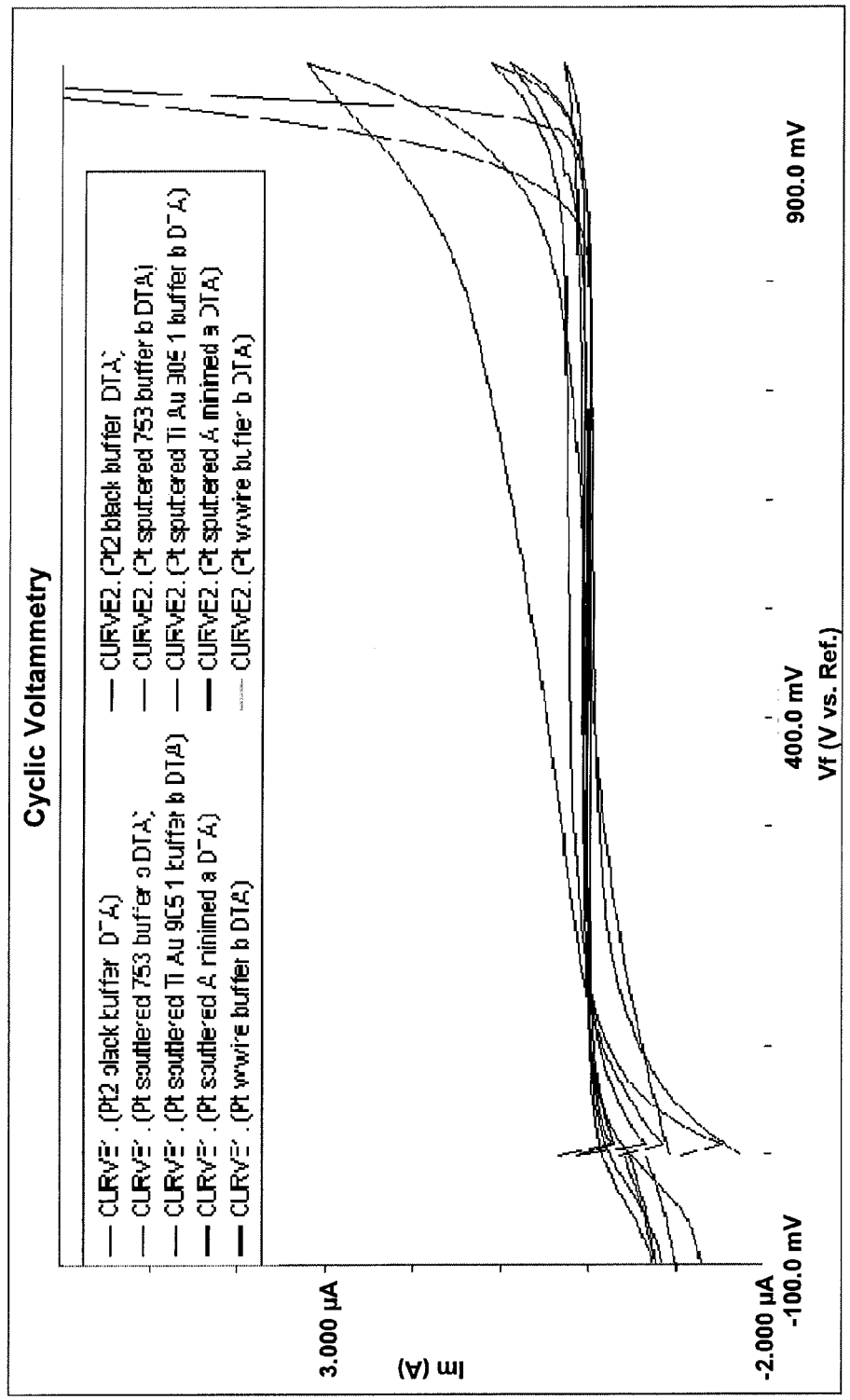
FIG. 5 provides graphs of cyclic voltammetry data showing comparisons of the background current generated by various platinum compositions.

FIG. 5 shows a comparison of background current observed with different platinum compositions. As shown in FIG. 5, the working electrode oxidation window for H2O2 is approximately from 500 mv to 800 mv. The background current during that range for Pt black is significantly higher in the group. Background current for pure Pt wire appears higher is due to a bigger surface area, 6 times of standard sputtered Pt. The surface area of Pt black is also much higher than sputtered WE, which could be the reason for higher background current. For sputtered WE the background currents are all significantly lower and they basically fall within the same magnitude.

Figure 6:
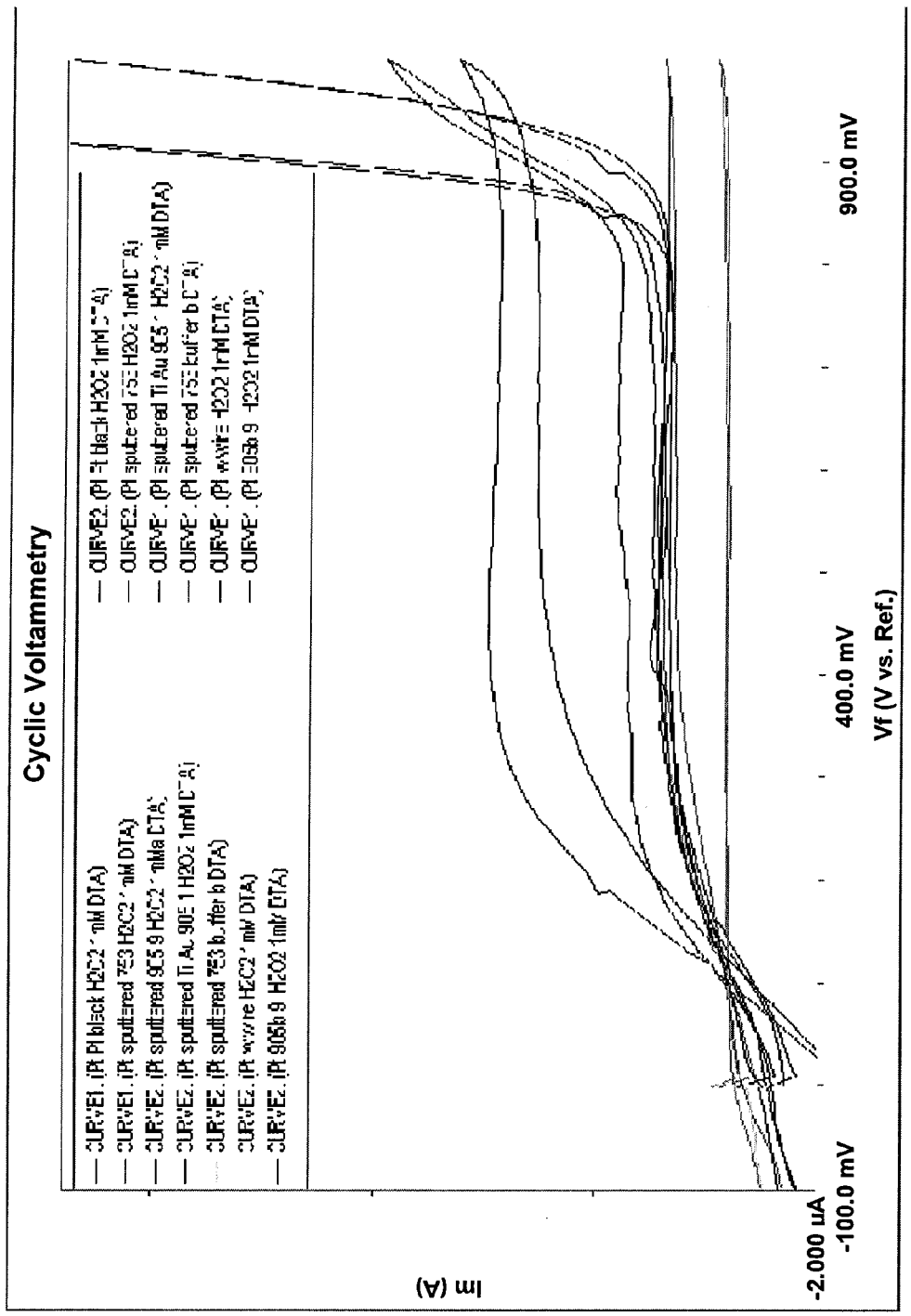
FIG. 6 provides graphs of cyclic voltammetry data for a comparison of overall electrocatalytic activity of all Pt sensors in 1 mM H2O2.

FIG. 6 shows a comparison of the electro-catalytic in response to 1 MM H2O2 observed with different platinum compositions. As shown in FIG. 6, Pt black did not show significantly higher electro-catalytic activity although did bring in a much higher background current. 1.75 WE basically provided the same Isig level with standard Platinum black sensor and lower background current. The Isig level from sputtered Pt is slightly lower than Pt wire and performance is comparable as far as the overvoltage is concern. But for Isig stability and noise level Platinum wire is superior to the rest of the Pts in group.

Typically a voltage at around 0.7V should be chosen as a H2O2 sensor for all of the Pts tested since some issue at higher H2O2 concentrations if using 0.5 to 0.6V range. It still works if H2O2 concentration is not over 2 mM level as long as a good linearity is obtained. Considering an extremely high glucose level at 50 mM, the H2O2 level could be just 1 mM in front of the WE. So a lower working potential is feasible for a number of applications.

Interference Responses to Acetaminophen

Figure 7:
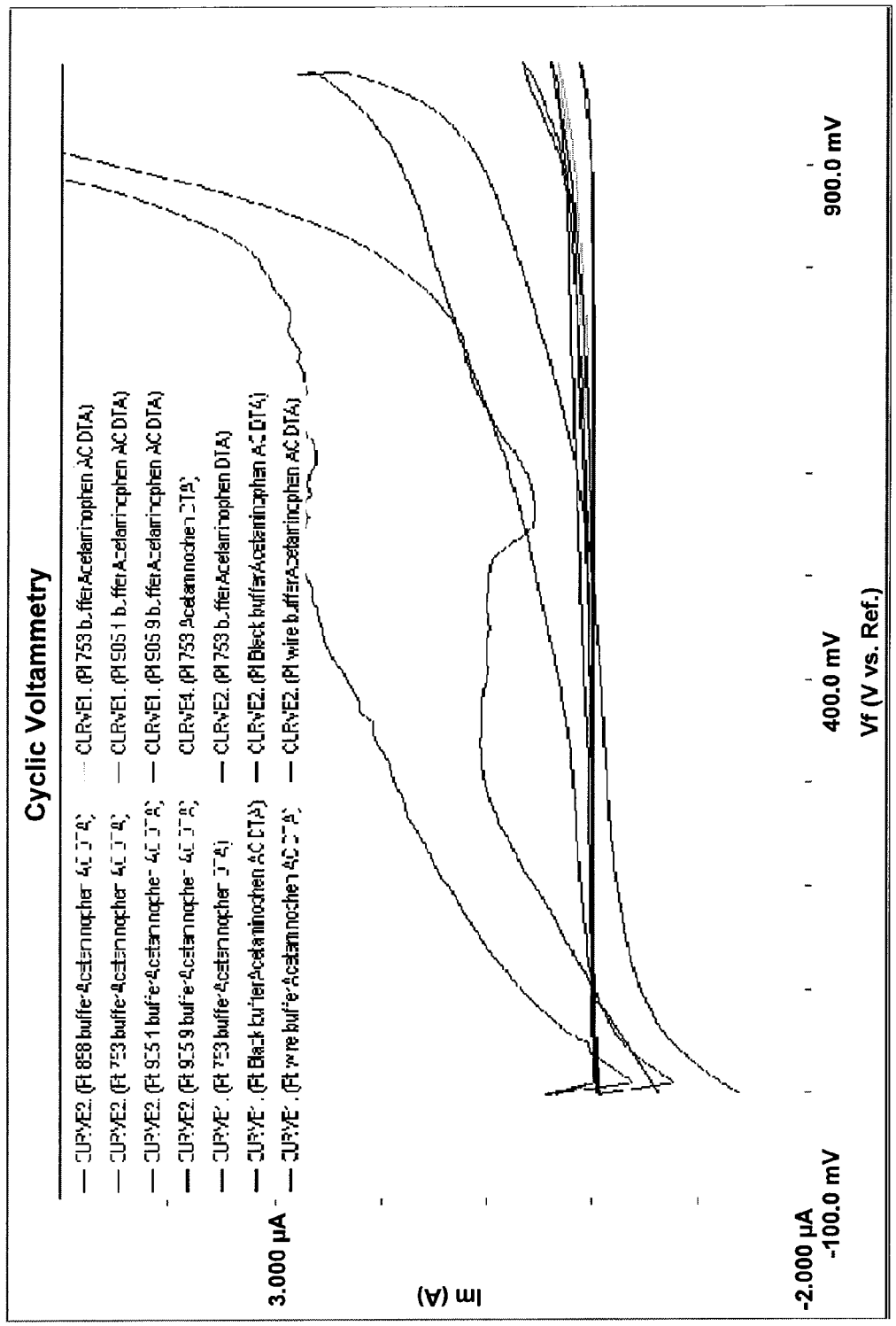
FIG. 7 provides graphs of data from studies of the effects of exposure to Acetaminophen on all Pt electrodes.

FIG. 7 shows the response of observed with different platinum compositions to the interferents acetaminophen. As shown in FIG. 7, interference from acetaminophen for sputtered Pt is lower overall. Pure Pt wire appears higher could be due to a higher surface area. But for Pt black the interference is significantly higher comparing the Isig level to H2O2.

In summary, the electrochemical characteristics of the sputtered Pt electrodes exhibit a better performance profile over Pt electrodes formed from different processes. For example, the Isig to background current and interference level while the O2 evolution apparently is suppressed, and the electrode electrocatalytic activity is still kept at the same level as pure Pt wire of the same surface area although a little worse noise level and signal stability. The Isig level is very consistent lot by lot. There is no significant difference between different designed patterns either. But the overall sweep performance appears from Lot753, standard 2x3x with Cr/Au as substrate perform the best. Slightly better performance was obtained with Cr/Au substrate over the TI/Au substrate as far as the background current and interference is concerned.

Example 3

Modification of Crosslinked SbQ Polymer Compositions by Plasma Deposition Processes As is known in the art, SbQ moieties on water soluble photosensitive poly(vinyl alcohol)-styrylpyridinium (PVA-SbQ) polymers are crosslinked when exposed to UV light (see, e.g. U.S. Pat. Nos. 7,252,912 and 6,379,883). As noted above, in certain embodiments of the invention, these UV crosslinked PVA-SbQ polymers are used to entrap glucose oxidase within one or more of the layers within a layered sensor architecture (e.g. a protein layer, an electrolyte retaining layer, an analyte sensing layer etc.). Embodiments of the invention comprise sensor layers made from this material, embodiments which can eliminate the need for the use of other cross linkers (such as glutaraldehyde) in sensor fabrication. For example, glutaraldehyde is the most commonly used crosslinker for proteins or enzymes. Problems with the use of this compound however include the observation that the sensor signal tends to decrease in response to continuing glutaraldehyde crosslinking because of its interaction with glucose oxidase and the existence of residual crosslinker in the sensor membrane matrix.

As disclosed herein, a new process comprising the use of a UV crosslinked polymer matrix to immobilize polypeptides such as GOx in combination with a plasma crosslinking and deposition methodology has been developed in order to eliminate the need for chemical crosslinkers such as glutaraldehyde in glucose sensor fabrication. The performance of sensors made in this way is comparable with that obtained with sensors made with standard glutaraldehyde crosslinking processes. In embodiments of the invention, GOx can be entrapped within this polymer matrix, a sensor architecture that results in sensors having analyte sensing layers that result in enhanced Isig quality in regards to sensor stability, linearity and diminished noise levels. In certain embodiments of the invention, this matrix functions as an electrolyte retaining layer (e.g. in combination with an electrode comprising a sputtered Pt composition).

As a dry and clean process, plasma methods offer advantages over wet crosslinking processes with an appropriate polymer matrix to be processed. For example, plasma deposition processes can be used in PVA-SbQ crosslinking methods to offer a better adhesion between sensor layers. Moreover, plasma processes can be focused to penetrate limited thickness of the top skin layer of a GOx composition matrix. Such thin plasma crosslinked layers can further enclose the GOx and prevent possible run out due to the limitation of PVA-SbQ GOx entrapment matrix. In illustrative embodiments of the invention, He and Ar plasma processes can be used to can crosslink a number of matrices, and HMDSO or HMDSO/allylamine plasma-enhanced chemical vapor deposition plasma processes can be used to produce pin-hole free films with adhesive functionalities. As is known in the art, plasma layers may be applied via a number of processes, including plasma polymerized hydrocyclosiloxane monomers, amine-providing groups such as N-trimethylsilyl-allylamine (allylamine), polyoxyalkylene tethers, and bioactive compounds (see, e.g. U.S. Pat. Nos. 6,613,432; 6,765,069 and 7, 217,769).

Plasma processes useful with embodiments of the invention can include a variety of methodologies such as radiofrequency plasmas (e.g., capacitively coupled plasmas, inductively coupled plasmas, helicon plasmas, etc.) and microwave plasmas (e.g., electron cyclotron resonance plasmas, etc.), among others. Various energetic species are associated with plasmas, including ions, electrons and photons (including UV photons). Where the magnitude of the energy transfer from the plasma is higher than the binding energy of certain orbital electrons in the polymer, the polymer surface will be activated while the precursor will be ionized, leading to molecular fragmentation into small fragments that contain free radicals. Where the magnitude of the energy transfer from the plasma is lower than the binding energy, on the other hand, certain electrons in the polymer are raised to an excited upper orbital, followed by dissociation, producing radicals at the polymer surface (see, e.g., N. Inagaki, Ph.D., Plasma Surface Modification and Plasma Polymerization). Illustrative processes comprising plasma surface modification are described in N. Inagaki, Plasma Surface Modification and Plasma Polymerization, Technomic Publishing Company, Inc. 1996; and L. Hanley et al., "The growth and modification of materials via ion-surface processing", Surface Science 500, 2002. Illustrative processes comprising vapor deposition are described in Smith, Donald (1995): Thin-Film Deposition: Principles and Practice. MacGraw-Hill; and Bunshah, Roitan F. (editor). Handbook of Deposition Technologies for Films and Coatings: Science, Technology and Applications, second edition. Materials science and process technology series. Park Ridge, N.J.: Noyes Publications, 1994.

Illustrative Plasma Process Summary

The basic processes use dry and clean plasma/plasma deposition to secure the UV cross linked GOx layer and to replace current wet chemistry adhesion promoter (AP) process. An exemplary process is summarized below in the following illustrative steps:

Secure a UV cross linked GOx layer with mild Helium plasma process (e.g. 50 W, 300 mT, 20 sec). Such finely tuned Helium plasma processes exhibit polymer surface crosslinking effects.

Create a very thin film on top of the plasma treated GOx through allylamine/HMDSO pulse plasma deposition (e.g. allylamine/HMDSO (1/1), 200 W, 350 mT, 2 min, and 30% of pulse duty cycle). According to difference requirements, the allylamine to HMDSO ratios are adjustable. For example, in some cases, HMDSO can be 100%. The chemical precursors can provide siloxane groups and amino functional groups that current adhesion promoter (3-aminopropyltriethoxysilane) can provide, but don't have issues related to the current APTES, such as low vapor pressure and very sensitive to moisture in the air. In fact, rather than liquid phases of those two monomers (precursors), their vapors are used, and each vapor produces a unique plasma composition resulting in unique surface properties. During the pulse plasma deposition process, the allylamine and HMDSO monomer vapors undergo fragmentation and reacts with the substrate and also with themselves to combine into pinhole-free films. HMDSO pulse plasma deposition generates sticky silica like thin film to bind to the substrate, which can provide a barrier to secure the GOx layer underneath and to further limit glucose permeation from glucose limiting membrane (GLM) layer on the top. Allylamine precursors can form hydrophilic membranes and also provide amino function groups to chemically bind the GLM cover layer.

After these steps, about 2 minutes of plasma pulse deposition, stronger helium plasma (e.g. 200 W, 350 mTorr, 70 seconds) can be used to cross link the newly deposited layer. This process increases the stability the deposition. O2 plasma oxidization is another option for the post plasma deposition treatment for some cases.

After these steps, one can wash the plasma processed plates for 5 minutes with DI water in a wash station and dry those plates with spin dry equipment. The purpose of this step is to remove chemical residues.

After the wash/dry step, GLM cover layer can be directly coated on to the treated plates.

Applying plasma/plasma deposition technology to implantable glucose sensor fabrication is an unique feature of the invention.

Illustrative Plasma Process Parameters

A. Illustrative Process A: 20 sec He crosslink @50 w, 2 min Allylamine/HMDSO (50/50 sccm) plasma deposition @200 w, followed by 70 s He crosslink @200 w, rinse and dry.
B. Illustrative Process B: 20 sec He crosslink @50 w, 3 min HMDSO(80 sccm) plasma deposition @200 w, followed by 10 sec of O2 plasma @10 w.
C. Illustrative Process C: 4 min HMDSO 80 sccm, 350 mtorr 200 w pulse followed by 10 s O2 @25 sccm 100 mtorr @10 w.

Following the processes discussed above, experiments show that SbQ-UV crosslinked GOx layers yield sensors having a number of desirable characteristics including greater responsiveness, less noise, and a more stable Isig. In addition, such processes can be used to enhance the performance of sensors comprising an interference rejection membrane.

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An amperometric analyte sensor apparatus comprising:
   a base layer;
   a conductive layer disposed on the base layer and comprising a working electrode;
   a first analyte sensing layer disposed over the conductive layer and comprising a first concentration of glucose oxidase;
   a second analyte sensing layer disposed over the first analyte sensing layer and comprising a second concentration of glucose oxidase;
   a third analyte sensing layer disposed over the second analyte sensing layer and comprising a third concentration of glucose oxidase; and
   an analyte modulating layer disposed over the first, second and third analyte sensing layers, wherein the first concentration of glucose oxidase is greater than the second concentration of glucose oxidase and the third concentration of glucose oxidase.

2. The analyte sensor apparatus of claim 1, wherein:
   the first concentration of glucose oxidase is between 35 KU/mL and 55 KU/mL;
   the second concentration of glucose oxidase is between 30 KU/mL and 55 KU/mL; or
   the third concentration of glucose oxidase is between 5 KU/mL and 15 KU/mL.

3. The analyte sensor apparatus of claim 1, wherein the analyte modulating layer comprises a blended mixture of a linear polyurethane/polyurea polymer and a branched acrylate polymer blended together at a ratio of between 1:1 and 1:20 by weight %.

4. The analyte sensor apparatus of claim 3, wherein the analyte modulating layer comprises a blended mixture of:

(1) a polyurethane/polyurea polymer formed from a mixture comprising:
   (a) a diisocyanate;
   (b) a hydrophilic polymer comprising a hydrophilic diol or hydrophilic diamine; and
   (c) a siloxane having an amino, hydroxyl or carboxylic acid functional group at a terminus; and
(2) a branched acrylate polymer formed from a mixture comprising:
   (a) a butyl, propyl, ethyl or methyl-acrylate;
   (b) an amino-acrylate;
   (c) a siloxane-acrylate; and
   (d) a poly(ethylene oxide)-acrylate.

5. The analyte sensor apparatus of claim 1, wherein the analyte modulating layer exhibits a permeability to glucose that changes less than 2% per degree centigrade over a temperature range of 22 to 40 degrees centigrade.

6. The analyte sensor apparatus of claim 1, further comprising at least one of:
   a protein layer;
   an interference rejection membrane;
   an adhesion promoting layer; or
   a cover layer disposed over the analyte sensor apparatus, wherein the cover layer comprises an aperture positioned on the cover layer so as to facilitate an analyte present in the mammal contacting and diffusing through an analyte modulating layer; and contacting the analyte sensing layer.

7. A composition of matter comprising:
   a metallic electrode;
   a first analyte sensing layer disposed over the metallic electrode and comprising a first concentration of glucose oxidase;
   a second analyte sensing layer disposed over the first analyte sensing layer and comprising a second concentration of glucose oxidase;
   a third analyte sensing layer disposed over the second analyte sensing layer and comprising a third concentration of glucose oxidase; and
   an analyte modulating layer disposed over the first, second and third analyte sensing layers, wherein the first concentration of glucose oxidase is greater than the second concentration of glucose oxidase and the third concentration of glucose oxidase.

* * * * *